United States Patent [19]

Peters et al.

[11] Patent Number: 4,980,279
[45] Date of Patent: Dec. 25, 1990

[54] CELLULAR FIBRONECTIN: POLYPEPTIDES, ANTI-POLYPEPTIDE ANTIBODIES AND ASSAY METHODS

[75] Inventors: John H. Peters, La Jolla; Mark H. Ginsberg, San Diego; Charles G. Cochrane, La Jolla, all of Calif.

[73] Assignee: Scripps Clinic and Research Foundation, La Jolla, Calif.

[21] Appl. No.: 852,127

[22] Filed: Apr. 15, 1986

[51] Int. Cl.$^5$ .................. G01N 33/53; G01N 33/566; G01N 33/00
[52] U.S. Cl. ........................................ 435/7; 436/501; 436/547; 436/548; 436/87; 530/395
[58] Field of Search ................. 436/501, 548, 547, 87, 436/435, 530; 435/7, 68; 530/324, 325, 326, 327, 328, 395

[56] References Cited

PUBLICATIONS

Kornblihtt, A. R. et al., EMBO J., vol. 3, No. 1, pp. 221-226 (1984).
Schoen, R. C. et al., Hybridoma, vol. 1, No. 2, pp. 99-108, (1982).
Lerner, R. A., Nature, vol. 299, pp. 592-596 (1982).
Paul et al., J. Biol. Chem., 261:12258-12265 (1986).
Berzofsky, Science, 229:932-940 (1985).
Barlow et al., Nature, 322:747-748 (1986).
Keen et al., Mol. Biol. Med., 2:15-27 (1984).
White et al., Principles of Biochemistry, Sixth Ed., McGraw-Hill Book Co., New York (1978) p. 140.
Borsi et al., J. Cell. Biol., 104:595-600 (1987).

Primary Examiner—Robert J. Warden
Assistant Examiner—Toni R. Scheiner
Attorney, Agent, or Firm—Dressler, Goldsmith, Shore, Sutker & Milnamow, Ltd.

[57] ABSTRACT

A synthetic polypeptide is disclosed that substantially corresponds in sequence to a portion of the amino acid residue sequence of the 90 amino acid residue extra type III domain of human cellular fibronectin from about position 36 to about position 60 from the amino-terminus. The polypeptide contains about 10 to about 25 amino acid residues. Also disclosed are antibodies and methods of using both the polypeptide and antibodies.

9 Claims, 2 Drawing Sheets

CELLULAR FIBRONECTIN: POLYPEPTIDES, ANTI-POLYPEPTIDE ANTIBODIES AND ASSAY METHODS

This invention was made with the support of the U.S. Government, and the U.S. Government has certain rights in the invention.

TECHNICAL FIELD

The present invention relates to human cellular fibronectin, and more specifically to polypeptides whose sequences correspond to a relatively unique portion of that molecule, antibodies to those polypeptides and methods for detecting human cellular fibronectin.

BACKGROUND

Oxidants accumulate at sites of tissue inflammation involving neutrophils. Cochrane at al., *J. Clin. Invest.* 71:754–61 (1983); Ward et al., *J. Clin. Invest.* 72:789–801 (1983). The ability of antioxidants to block physiologic and morphologic disruption at these sites suggests that oxidants contribute to neutrophil-associated tissue injury. Ward et al., *J. Clin. Invest.* 72:789–801 (1983); Till et al., *J. Clin. Invest.* 69:1126–35 (1982). However, oxidants probably cooperate with other inflammatory effector agents, including proteases, to cause tissue injury in vivo. Schraufstatter et al., *J. Clin. Invest.* 73:1175–84 (1984); Revak et al., *J. Clin. Invest.* 76(3):1182–92; Lee et al. *N. Engl. J. Med.* 304:192–196 (1981); McGuire et al. *J. Clin. Invest.* 69:543–53 (1982). In order to assay the effects of antioxidants and antiproteases in experimental animals and humans, effector-specific biochemical markers of tissue injury are needed. Ideally, those markers should be soluble and present in blood and/or other accessible body fluids.

Fibronectins are large glycoproteins found in plasma, on cell surfaces, and in extracellular matrices. By binding other macromolecules as well as cells, they serve to promote anchorage of cells to substrata. Cochrane et al., *J. Clin. Invest.* 1:754–61 (1983); Hynes et al. *J. Cell Biol.* 5:369–77 (1982). Fibronectins are composed of subunits of variable primary structure [average relative molecular mass 250 kilodaltons (kDa)], that are disulfide-linked to form dimers or multimers. Hynes, in *Cell Biology of the Extracellular Matrix*, Hay ed., Plenum Press, pages 295–334 (1982); Hynes, et al., *Cell Biol.* 95:369–77 (1982); Ruoslahti et al. *Meth. Enzy.* 82:803–30 (1982); Schwarzbauer et al. *Proc. Natl. Acad. Sci. USA* 82:1424–28; Kornblihtt et al. *EMBO J.*, 4(7):1755–59 (1985). Plasma fibronectin (PFn) is secreted by hepatocytes, whereas cellular fibronectin (CFn) is secreted by a variety of cultured cells including endothelial cells and fibroblasts. Tamkun et al. *J. Biol. Chem.* 58(7):4641–47; Jaffe et al. *J. Exp. Med.* 147:1779–91 (1978); Birdwell, et al. *Biochem. Biophys. Res. Commun.* 97(2):574–8 (1980). Despite extensive physical and immunologic similarities, the two classes of fibronectin differ in electrophoretic behavior, solubility, and biologic activities. Tamkun et al., *J. Biol. Chem.* 258(7):4641–47 (1983); Yamada et al., *J. Cell Biol.* 80:492–98 (1979); Yamada et al. *Biochemistry* 16(25):2552–59 (1977).

Primary structural differences between plasma and cellular fibronectins have been found by peptide mapping [Hayashi et al. *J. Biol. Chem.* 256(21):11,292–11,300 (1981)] and immunologic techniques [Atherton et al. *Cell* 25:133–41 (1981)]. Recently, a difference region encoding for exactly one 90 amino acid type III structural repeat was identified in mRNA from human fibroblasts and two human tumor cell lines, but could not be detected in human liver mRNA. Kornblihtt et al. *EMBO J.* 4(7):1755–59 (1985); Kornblihtt et al., *EMBO J.* 3(1):221–26 (1984); Kornblihtt et al., *Nucleic Acids Res.* 12(14):5853–68 (1984). Since plasma fibronectin is synthesized by hepatocytes, it is likely that the extra type III repeat is a unique domain of cellular fibronectins. Schwarzbauer et al., *Proc. Natl. Acad. Sci. USA.*, 82:1424–28 (1985); Kornblihtt et al., *EMBO J.* 3(1):221–26 (1984); Kornblihtt et al., *Nucleic Acids Res.* 12(14):5853–68 (1984).

Fibronectin accumulates at sites of injury and inflammation in vivo [Pettersson et al., *Clin. Immunol. Immunopath* 11:425–436 (1978); Grinnel et al. *J. Invest. Derm.* 76:181–189 (1981); Repesh et al. *J. Histochem. Cytochem.* 30(4):351–58 (1982); Torikata et al., *Lab. Invest.* 52(4):399–408 (1985); Carsons et al. *Arth. Rheum* 24(10):1261–67 (1981)] and is produced by cells in blood vessel walls at these sites. Clark et al., *J. Exp. Med.* 156:646–51 (1982); Clark et al., *J. Immunol.* 126(2):787–93 (1981); Clark et al., *J. Invest. Derm.* 79:269–76 (1982); Clark et al., *J. Clin. Invest.* 74:1011–16 (1984).

Cellular fibronectin might accumulate in the vascular compartment and in other fluids in communication with sites of inflammatory tissue injury. Studies discussed in detail hereinafter were carried out using mediators of inflammatory tissue injury, including oxidants and proteases, to promote in situ release of cellular fibronectin. We chose to perform our studies in an in vitro perfused rabbit lung, since this model provides an abundantly vascular tissue that can be observed for both physiologic and biochemical changes under defined conditions.

BRIEF SUMMARY OF THE INVENTION

The present invention contemplates a synthetic polypeptide that corresponds substantially in sequence to a portion of the amino acid residue sequence of human cellular fibronectin, antibodies to those polypeptides, as well as to assay methods that utilize those antibodies and polypeptides.

One aspect of the invention contemplates a synthetic polypeptide containing about 10 to about 25 amino acid residues, and more preferably about 15 to about 20 residues, that corresponds substantially in sequence to the 90 amino acid residue extra type III domain of human cellular fibronectin from about position 36 to about position 60 from the amino-terminus. Particularly preferred synthetic polypeptides have a sequence, from left to right and in the direction from amino-terminus to carboxy-terminus, of:

(a) ELFPAPDGEEDTAELQG, and
(b) TYSSPEDGIHELFPAPDGEEDTAELQG,
    using single-letter abbreviations.

A composition of a physiologically tolerable diluent containing an effective amount of a synthetic polypeptide of this invention linked to an immunogenic carrier as a conjugate when introduced into a host animal, is capable of inducing the secretion of antibodies that immunoreact with the immunizing polypeptide, cellular human fibronectin in the denatured state, and more preferably, also in the native, non-denatured state, about are substantially free from immunoreaction with native and denatured human plasma fibronectin.

Another aspect of the invention contemplates a preparation of antibodies induced by a synthetic polypeptide of the invention. Those antibodies immunoreact with a synthetic polypeptide of this invention and denatured human cellular fibronectin, and preferably also immunoreact with native, non-denatured human cellular fibronectin, but do not substantially immunoreact with human plasma fibronectin in either the denatured or native states. The antibodies can be present in the serum of the host animal, and can also be in substantially pure form, substantially free of host serum proteins, polypeptides and cellular debris.

Yet another aspect of the present invention contemplates an assay method. In one assay method, the amount of cellular fibronectin in a body sample can be determined, while in another embodiment, the total amount of fibronectin, as well as cellular and plasma fibronectin portions of total fibronectin are determined.

In the first assay method, anti-polypeptide antibodies of this invention that immunoreact with native human cellular fibronectin are affixed to a solid matrix to form a solid phase support. A predetermined amount of a liquid body sample to be assayed for human cellular fibronectin is admixed with the solid phase support to form a solid-liquid phase admixture. The solid-liquid phase admixture so formed is maintained for a predetermined time period sufficient for human cellular fibronectin present in the sample to immunoreact with the solid phase-affixed antibody and form a solid phase-bound immunoreactant and a liquid phase depleted of human cellular fibronectin. The solid and liquid phases are separated, and the amount of solid phase-bound immunoreactant formed is determined. That determination can conveniently be made by admixing a sufficient amount of second antibodies that immunoreact with human cellular fibronectin in the presence of the first-named antibodies with the solid phase to form a second solid-liquid phase admixture. The second solid-liquid phase admixture is maintained for a time sufficient for the second antibodies to immunoreact with the solid phase-bound human cellular fibronectin. The second solid-liquid phase admixture is separated into its solid and liquid phases. The amount of second antibody bound to the solid phase is determined, thereby providing the amount of human cellular fibronectin in the sample. The amount of second antibody bound is conveniently determined by providing a label such as an enzyme operably linked to the second antibody.

The second assay method comprises two separate assays, assays (A) and (B) and is utilized to determine the amount of plasma fibronectin present in the sample to be assayed. Assay (A) is that described above. The total amount of fibronectin is determined in assay (B). There, for example, a second solid phase support is comprised of a solid matrix to which are affixed antibodies raised in a host animal that immunoreact with a human fibronectin epitope in addition to those of the type III domain of human cellular fibronectin. A second predetermined amount of the liquid body sample to be assayed is admixed and maintained to form a solid phase-bound immunoreactant, and the solid and liquid phases are separated as described before for assay (A). Thereafter, the amount of solid phase-bound immunoreactant, and thereby total fibronectin in the second amount of sample is determined. That determination is typically carried out by admixing a liquid composition containing second antibodies raised in a host animal that immunoreact with a human fibronectin epitope in addition to those of the type III domain of human cellular fibronectin in an amount sufficient to immunoreact with the fibronectin bound to the solid phase support to form a second solid-liquid phase admixture. That second admixture is maintained for a predetermined time sufficient for the second antibodies to immunoreact with the bound fibronectin, the solid and liquid phases are separated, and the amount of second antibodies bound to the solid phase are determined, thereby determining the total amount of fibronectin present in the sample. The amount of human cellular fibronectin determined from assay (A) is then subtracted from the total amount of fibronectin to provide a determination of the amount of plasma fibronectin present in the sample. The total amount of fibronectin in the sample; i.e., the amount of second antibody bound to the solid phase can also be conveniently determined by providing a label operably linked to the second antibody.

The present invention provides several benefits and advantages.

One benefit is that antibodies capable of distinguishing human cellular fibronectin from human plasma fibronectin can be prepared.

One advantage of the present invention is that the amount of human cellular fibronectin in a sample to be assayed can be determined in the presence of human plasma fibronectin.

Another benefit of the invention is that the amounts of human cellular and plasma fibronectins can both be determined.

Another advantage of the invention is that diagnosis and management of patients with fibrosing disorders such as scleroderma, cirrhosis, pulmonary fibrosis and glomerulonephritis can be achieved.

Still further benefits and advantages of the present invention will be apparent from the detailed description of the invention that follows.

BRIEF DESCRIPTION OF THE DRAWINGS

In the drawings that constitute a portion of this disclosure.

Figure 1:
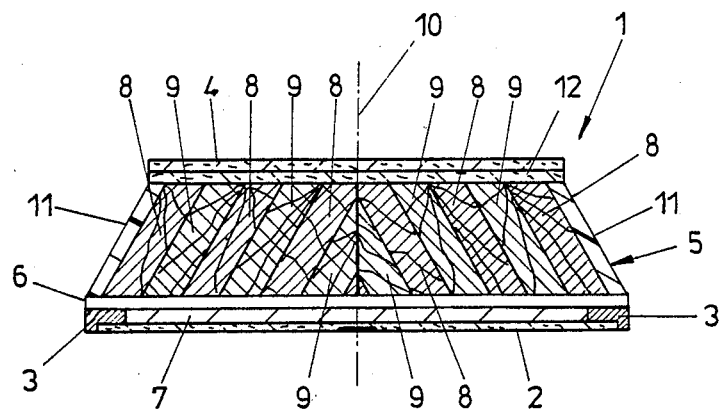
FIG. 1 illustrates Western blot analyses using human plasma fibronectin and human cellular fibronectin visualized by antibody preparations. Equal amounts of fibronectin purified from human plasma (Plas) and BM-1380 human fibroblast (Cell) media by gelatin affinity chromatography were subjected to SDS-PAGE (reducing conditions) and Western transfer in paired lanes. Staining was accomplished with (from left to right) anti-ED polypeptide serum, anti-ED polypeptide serum preincubated with ED polypeptide, and anti-plasma fibronectin antibodies. Because the fibroblast media contained fetal bovine serum, the electrophoretic mobility of bovine plasma fibronectin was also examined. The two arrows represent the positions at which the bovine plasma fibronectin doublet migrates. Visualization is as discussed in MATERIALS AND METHODS.

Panel A. Similar quantities of fibronectin were isolated on gelatin-agarose beads from: lane (1) heparin-urea extract of uninjured perfused (bloodless) rabbit lung tissue, lane (2) perfusion fluid obtained at 90 minutes from a rabbit lung injured by $H_2O_2$ infusion, and lane (3) rabbit plasma. The samples were reduced and electrophoresed on a 6 percent acrylamide gel.

B. Perfusion fluid from an $H_2O_2$-injured rabbit lung (lanes 1 and 3) and rabbit plasma fibronectin diluted in perfusion buffer (lanes 2 and 4) were subjected to 3-20 percent gradient SDS-PAGE under reducing (1 and 2) and ron-reducing (3 and 4) conditions. The fluids were subjected to electrophoresis without prior isolation of fibronectin.

FIG. 4 illustrates physical characteristics of fibronectin in perfusion fluid and lavage. Fibronectin was isolated on gelatin-agarose beads from serial aliquots of perfusate and BAL from representative rabbit lungs treated with xanthine oxidase plus purine (XO/P) or $H_2O_2$ infusion in the presence or absence of catalase. Sample and bead volumes were kept constant so that quantities of fibronectin isolated would reflect fibronectin concentration in perfusion fluid at time points. Samples and plasma fibronectin controls were subjected to prolonged electrophoresis in 5 percent gels followed by Western transfer with staining by anti-rabbit plasma fibronectin antibodies.

FIG. 5 illustrates the molecular weight distributions in fibronectin samples from a representative trypsin-injured rabbit lung. From left to right: plasma fibronectin standard (PLAS FN), serial perfusate samples (PERFUSATE), BAL, and SDS-extract of lung tissue (LUNG). Samples were boiled in SDS immediately after removal from the lung or in the case of lung tissue, after homogenization in a liquid nitrogen-cooled cartridge. Reduced samples of perfusate were then subjected to 3-20 percent SDS-PAGE and Western transfer. Staining was achieved with an approximately 10-fold greater concentration of anti-rabbit plasma fibronectin antibodies than used in FIG. 2, allowing visualization of fibronectin present in the perfusion fluid at the beginning of observation (i.e., time=0 minutes). This fibronectin had accumulated in perfusion fluid during the 30 minute equilibration period prior to the study. Numerals followed by the letter "K" at the left-hand side of the Figure illustrate the migration of materials of known relative molecular masses in kilodaltons.

Figures 6A, 6B:
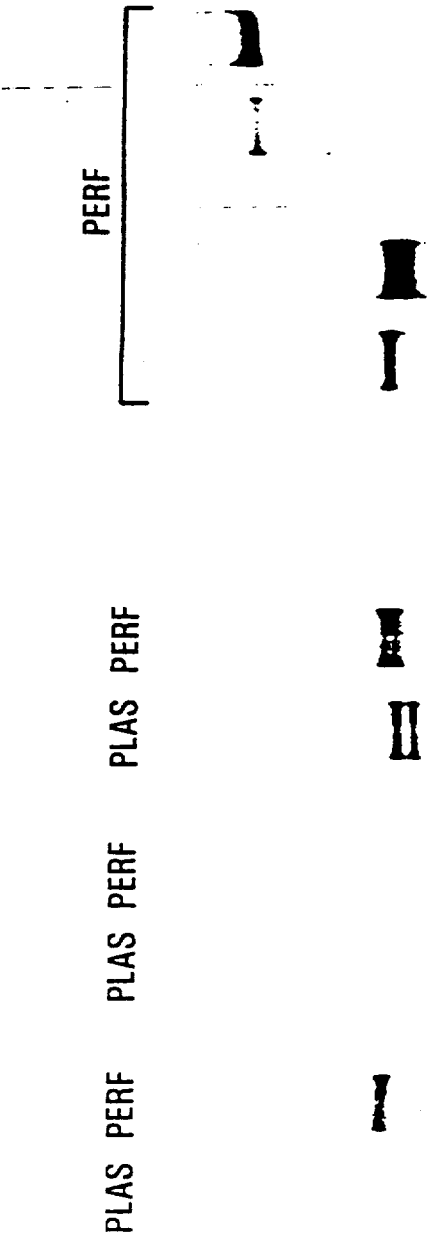

FIG. 6 illustrates that antibodies to an extra type III domain polypeptide of this invention react specifically with perfusate fibronectin. Equal amounts (measured by ELISA) of fibronectin isolated from rabbit plasma (PLAS) or perfusion fluid (PERF) obtained from $H_2O_2$-injured lungs at 90 minutes were subjected to prolonged 5 percent SDS-PAGE and Western transfer in parallel.

A. After electrophoresis under reducing conditions, electrophoretically transferred fibronectins were stained with anti-polypeptide serum (lanes 1 and 2), anti-polypeptide serum preincubated with polypeptide (lanes 3 and 4), or anti-rabbit plasma fibronectin antibodies (lanes 5 and 6).

B. Perfusate fibronectin under reducing (lanes 1 and 2) and non-reducing (lanes 3 and 4) conditions. Staining was achieved with anti-polypeptide serum (lanes 1 and 3) or anti-plasma fibronectin antibodies (lanes 2 and 4).

The polypeptide utilized to induce the production of the anti-polypeptide antibodies and for the preincubation had the amino acid residue sequence, from left to right and in the direction from amino-terminus to carboxy-terminus, of:

ELFPAPDGEEDTAELQG

Detailed Description Of The Invention

I. OVERVIEW

The data presented hereinafter (RESULTS) show that oxidant and protease-induced vascular injury are each associated with characteristic effector-specific changes in pulmonary tissue fibronectin in vitro.

Intact fibronectin dimers are released into blood vessels of isolated perfused rabbit lungs in response to levels of circulating oxidants that lie within the consumptive capabilities of lung antioxidant defenses. These levels of oxidants nevertheless cause vascular disfunction (evident as lung weight gain), and this process correlates temporally with fibronectin release. When subjected to electrophoresis, subunits of the released fibronectin migrate more slowly than those of rabbit plasma fibronectin. This is typical of human, chicken, rat, and hamster cellular fibronectins in comparison with their plasma counterparts. Tamkun et al., *J. Biol. Chem.* 258(7):4641-47 (1983); Yamada al., *J. Cell Biol.* 80:492-98 (1979); Quaroni et al., *Proc. Natl. Acad. Sci. USA.*, 75(11):5548-52 (1978). Additionally, the released fibronectin shows similar electrophoretic mobility to fibronectin extracted from normal rabbit lung tissue perfused free of blood elements. Therefore, the fibronectin released by the oxidant-injured vasculature of the in vitro perfused lung appears by electrophoretic comparisons to be cellular fibronectin (CFn).

To confirm the designation of perfusate fibronectin as cellular fibronectin the known differences in primary structure between non-hepatic (cellular) and hepatic (plasma) fibronectins [Kornblihtt, *EMBO J.*, 4(7):1755-59 (1985)] were exploited. The feasibility of this approach in the rat system was recently reported by Hynes who reported that antibodies to a relatively large fusion protein containing an extra type III repeat of rat fibronectin reacted with subunits of rat cellular but not rat plasma fibronectin.

Here, antibodies prepared to an amino acid residue sequence within the extra type III domain of human fibronectin reacted exclusively with human cellular but not plasma fibronectin. The reactivity of the antibodies of this invention with rabbit lung perfusate fibronectin also identifies that protein as cellular fibronectin, and illustrates the homology between the extra type III domains of rabbit and human cellular fibronectins.

Because fluid accumulation by the oxidant-injured lungs (measured as weight gain) accounted for less than 20% additional contraction of the recirculating volume, the greater than six-fold average increase in fibronectin concentration achieved in the circulation of these lungs compared with uninjured lungs must be attributed to intravascular release rather than concentration. The mechanism of vascular release of intact cellular fibronectin in response to oxidants remains unclear. Fibronectin could be dislodged from extracellular sites or released by cells in proximity to the vasculature.

The absence of detectable plasma fibronectin in perfusion fluid from oxidant-injured lungs suggests that oxidant stress does not lead to intravascular release of sequestered plasma proteins. It also discounts the possibility that the cellular fibronectin released by oxidant-exposed blood vessels could originally have been blood-derived from extrapulmonary tissues.

Because various mononuclear cells [Hynes et al. *J. Cell Biol.* 95:369-7 (1982)] as well as polymorphonuclear cells [Weissmann et al., *Assoc. Am. Phys.* 93:72-84 (1980); Menard et al. *Clin. Exp. Immunol.* 60:347-54 (1985)] have been shown to synthesize fibronectin, differences in perfusate concentrations of fibronectin between oxidant and control groups could conceivably arise from differences in cellular composition of perfusate or tissue. However, as noted hereinafter in Table III, significant differences in circulating cells were not apparent between these groups. Nor were there discernible differences in tissue cellularity as judged by light microscopy.

Endothelial cells, the major cell group in contact with the circulation in our model, secrete intact cellular fibronectic dimers into cell culture medium when grown in tissue culture. Jaffe, et al. *J. Exp. Med.* 147:1779-91 (1978); Birdwell, et al., *Biochem. Biophys. Res. Commun.* 97(2):574-8 (1980). Additionally, these cells have been shown to produce fibronectin in response to tissue injury and inflammation in vivo. Clark et al., *J. Exp. Med.* 156:646-51 (1982); Clark et al., *J. Immunol.* 126(2):787-93 (1981); Clark et al., *J. Invest. Derm.* 79:269-76 (1982); Clark et al., *J. Clin. Invest.* 74:11011-16 (1984). These facts, taken together with our data, suggest that endothelial cells are a potential site of release of fibronectin in response to oxidant stress.

The association of oxidant exposure with intravascular release of cellular fibronectin in the in vitro perfused rabbit lung illustrates that cellular fibronectin represents a soluble marker in blood or other accessible tissue fluids for oxidant-induced injury. Intact fibronectin, not characterized as to source, has been shown to accumulate in the circulation of rats exposed to hyperoxia. Glass, et al. *Amer. Rev. Resp. Dis.* 130:237-241 (1984). Because hyperoxia is associated with pulmonary tissue injury involving increased local oxidant production by lung tissue [Freeman et al., *J. Biol. Chem.* 256(21):13986-92 (1981); Turrens et al., *J. Clin. Invest.* 73:87-95 (1984)], the associated accumulation of circulating fibronectin could conceivably result, in the rats exposed to hyperoxia as in our models, from release of fibronectin by oxidant-injured pulmonary vasculature.

In contrast to the results obtained with oxidants, protease-induced vascular injury of the perfused lung was associated with decreased levels of circulating fibronectin measured by immunoassay (ELISA). However, Western blotting revealed that the samples subjected to ELISA did not contain intact fibronectin.

Whereas perfusate samples taken prior to addition of protease contained fibronectin with electrophoretic mobility consistent with intact cellular fibronectin, samples at later time points contained fibronectin that had been proteolytically degraded. Since proteolysis was shown to lead to decreased measured values by (LISA, fibronectin may have been proteolytically released from vessels, but not sensed by immunoassay due to diminished antigenicity.

The increased fibronectin levels in the lavage fluids from lungs with signs of vascular dysfunction (increased lung weight and lavage protein) appears to reflect movement of fluid and proteins from the circulation into the alveoli and/or local release of fibronectin from alveolar tissue or cells. Since the predominant protein that was detected in the airspaces of injured lungs comigrated with perfusion fluid containing BSA in SDS-PAGE, it is likely that fluid and proteins, including fibronectin, moved from the circulation to airspaces during vascular injury.

In summary, the results shown herein illustrate that oxidant and protease-induced vascular injury are each associated with characteristic alterations in fibronectin derived from non-hepatic tissue in vitro. Non-hepatic tissue fibronectin (cellular fibronectin) is therefore recognized as an in situ target of these two major classes of inflammatory effector agents. Additionally, a method for the assay of cellular (tissue) fibronectin to the exclusion of plasma fibronectin has been described. Thus, cellular tissue fibronectin can now be used as a probe for effector-specific tissue injury in vivo.

II. SPECIFICS

The present invention contemplates a synthetic polypeptide that corresponds substantially in sequence to a portion of the amino acid residue sequence of human cellular fibronectin, antibodies that immunoreact with those peptides, and methods of using the same.

A. Polypeptides and antibodies

One aspect of the invention contemplates a synthetic polypeptide that contains a sequence of about 10 to about 25 amino acid residues, and more preferably about 15 to about 20 residues. The polypeptide corresponds substantially in sequence to the 90 amino acid residue extra type III domain of human cellular fibronectin from about position 36 to about position 60 from the amino-terminus.

The full names for individual amino acid residues are sometimes used herein as are the well-known three-letter abbreviations. Single-letter abbreviations (code) is most often utilized. The Table of Correspondence, below, provides the full name as well as the three-letter and single-letter abbreviations for each amino acid residue named herein (See, for example, L. Stryer, *Biochemistry*, 2nd ed., W. H. Freeman and Company, San Francisco, (1981), page 16.). The amino acid residues utilized herein are in the natural, L, form unless otherwise stated.

| Table of Correspondence | | |
|---|---|---|
| Amino acid | Three-letter abbreviation | One-letter symbol |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |

-continued

Table of Correspondence

| Amino acid | Three-letter abbreviation | One-letter symbol |
| --- | --- | --- |
| Valine | Val | V |

Particularly preferred synthetic polypeptides of the invention have a sequence, from left to right and in the direction from amino-terminus to carboxy-terminus, of:
 (a) ELFPAPDGEEDTAELQG, and
 (b) TYSSPEDGIHELFPAPDGEEDTAELQG,
using single-letter abbreviations.

The sequence of polypeptide (a) above is that from positions 45 through 61 of the 90 residue extra type III repeat domain determined from the amino-terminus of the domain. The sequence of polypeptide (b) above is that from positions 36 through 61 of that 90 residue domain measured the same way. For use herein, additional gly-cys residues were added to the carboxy-terminus of each polypeptide to assist in linkage of the polypeptide to the solid support during syntheses.

The polypeptide whose sequences is shown in (a), above, along with its added carboxy-terminal gly-cys residues is sometimes referred to herein as the extra domain (ED) polypeptide.

Throughout the application, the terms "peptide" and "polypeptide" are used interchangeably. The term "synthetic polypeptide" means a chemically built-up, as compared to a biologically built and degraded, chain of amino acid residues that is free of naturally occurring proteins and fragments thereof. Such synthetic polypeptides can elicit production of anti-polypeptide antibodies in a host, and are conveniently synthesized by well known methods.

The term "substantially corresponds" in its various grammatical forms is used herein and in the claims in relation to polypeptide sequences to mean the polypeptide sequence described plus or minus up to three amino acid residues at either or both of the amino- and carboxy-termini and containing only conservative substitutions in particular amino acid residues along the polypeptide sequence.

The term "conservative substitution" as used above is meant to denote that one amino acid residue has been replaced by another, biologically similar residue. Examples of conservative substitutions include the substitution of one hydrophobic residue such as Ile, Val, Leu or Met for another, or the substitution of one polar residue for another such as between Arg and Lys, between Glu and Asp or between Gln and Asn, and the like.

In some instances, the replacement of an ionic residue by an oppositely charged ionic residue such as Asp by Lys has been termed conservative in the art in that those ionic groups are thought to merely provide solubility assistance. In general, however, since the replacements discussed herein are on relatively short synthetic polypeptide antigens, as compared to a whole protein, replacement of an ionic residue by another ionic residue of opposite charge is considered herein to be "radical replacement", as are replacements between nonionic and ionic residues, and bulky residues such as Phe, Tyr or Trp and less bulky residues such as Gly, Ile and Val.

The terms "nonionic" and "ionic" residues are used herein in their usual sense to designate those amino acid residues that normally either bear no charge or normally bear a charge, respectively, at physiological pH values. Exemplary nonionic residues include Thr and Gln, while exemplary ionic residues include Arg and Asp.

A polypeptide of the present invention is preferably linked to an immunogenic carrier such as a protein as a conjugate for use in production of antibodies and antibody preparations. Immunogenic carriers are well known in the art and include keyhole limpet hemocyanin (KLH), edestin, curcubin, human serum albumin, tetanus toxoid, sheep erythrocytes, polyamino acids such as poly(D-lysine D-glutamic acid) and the like. KLH is utilized herein as an exemplary immunogenic protein carrier.

Methods of linking the polypeptide to the immunogenic carrier to form the conjugate are also well known. Exemplary techniques include use of glutaraldehyde, a water-soluble carbodiimide, and those described in U.S. Pat. No. 4,544,500 and U.S. Pat. No. 4,545,931, whose disclosures are incorporated by reference.

The polypeptide-carrier conjugate is dissolved or dispersed in an aqueous composition of a physiologically tolerable diluent when used to induce the production of antibodies. Suitable physiologically tolerable diluents are well known in the art and include phosphate-buffered saline (PBS) and 0.9 normal saline, and preferably also include an adjuvant such as complete Freund's adjuvant or incomplete Freund's adjuvant.

An effective amount of a conjugate-containing composition is introduced into a host animal such as a goat, rabbit, mouse, rat, horse or the like to induce the production (secretion) of antibodies to the polypeptide. Methods of introduction into the host animal are also well known and are typically carried out by parenteral administration as by injection. A plurality of such introductions is normally utilized so that the host is hyperimmunized to the immunogenic polypeptide-containing conjugate. For example, weekly introductions over a one-to-two-month time period can be utilized until a desired anti-polypeptide antibody titer is achieved.

The antibodies so induced are thereafter recovered from the host animal. The recovered antibodies can be utilized as a preparation in the host serum as recovered, or can be in substantially pure form; i.e., substantially free from host serum proteins, polypeptides and cellular debris. The latter antibody preparation can be conveniently prepared by passage of the recovered serum over an affinity column as prepared from Sepharose 4B (Pharmacia Fine Chemicals, Piscataway N.J.) linked to the polypeptide of the conjugate, as is known.

The preparation of antibodies immunoreacts with a synthetic polypeptide of the invention, such as the polypeptide of the conjugate, as well as with denatured human cellular fibronectin. In more preferred practice, the antibodies also immunoreact with native, non-denatured human cellular fibronectin as is present in human plasma and serum. The antibodies are substantially free from immunoreaction with native human plasma fibronectin, and also with denatured human plasma fibronectin. Thus, the antibodies of the present invention do not cross-react with human plasma fibronectin (PFn).

An antibody preparation of this invention can be in dry form as obtained by lyophilization. However, the antibodies are normally used and supplied in an aqueous liquid composition in serum or a suitable buffer such as PBS.

B. Assay Methods

The antibodies and polypeptides described herein are useful in assay methods for the determination of the presence and amount of human cellular fibronectin (CFn).

The polypeptides are particularly useful in these assays for blocking studies as are described in connection with the Western blot-type assays described hereinafter. Similar blocking can also be carried out in solid phase assays such as the ELISA-type studies that are also described hereinafter.

The antibodies are particularly useful in assays because of their unique specificity for immunoreacting with human CFn. For example, tissue samples from patients having or suspected of having fibrosing disorders such as scleroderma, cirrhosis, pulmonary fibrosis and glomerulonephritis can be admixed and contacted with the antibodies. After passage of a predetermined maintenance time for the contact, the tissue sample is rinsed to remove any antibodies that did not immunoreact. The immunoreacted antibodies are thereafter visualized or with labeled second antibodies that bind to the first antibodies, or label-linked *S. aureus* Cowan strain protein A, or a visualizing label can be linked directly to the antibodies of the invention.

Solid phase assays, such as enzyme-linked immunosorbant assays (ELISA), radio-labeled immunosorbant assays (RIA) or flurochrome-linked immunosorbant assays (FIA) are also particularly useful. The ELISA technique is utilized herein as exemplary.

Thus, the amount of CFn present in a body sample is assayed in one embodiment of this invention. Here, a solid phase matrix such as the sides and bottom of a polystyrene or polyvinylchloride microtiter plate is provided. Antibodies of this invention are affixed to the solid matrix as by physical binding to form a solid phase support, as is known.

A predetermined amount of a liquid body sample such as plasma or serum to be assayed for human CFn is admixed with the solid phase support to form a solid-liquid admixture. Exemplary predetermined amounts typically are about 25 to about 150 microliters neat, or more preferably present at a known dilution in an aqueous medium such as PBS that contains a total volume of about 25 to about 150 microliters.

That solid-liquid admixture is maintained for a period of time sufficient for human CFn present in the sample to immunoreact with the solid phase-affixed antibody to form a solid phase-bound immunoreactant, and a liquid phase depleted of human CFn. Exemplary maintenance (incubation) times typically range from about 1 to about 6 hours, with the temperature of that maintenance typically being from about room temperature (about 20° C.) to about 40° C.

The solid and liquid phases are then separated as by rinsing to remove any materials from the sample that were not bound to the solid support. The solid phase containing the bound immunoreactant is retained for further use in the assay.

The amount of solid Phase-bound immunoreactant formed is then determined, and thereby determines the amount of CFn present in the assayed sample. That amount can be determined in a number of well known manners.

For example, where the amount of antibodies affixed to the solid matrix is known, a polypeptide of this invention operably linked to a label (labeling means) can be immunoreacted with the unreacted affixed antibodies, and the amount of immunoreactant determined by difference.

More usually, the amount of solid phase-bound immunoreactant is conveniently determined by admixing an amount of second antibodies that is sufficient to immunoreact with the bound CFn to form a second solid-liquid phase admixture. Those second antibodies must of course bind to the CFn in the presence of the antibodies affixed to the solid matrix. Exemplary of such antibodies are polyclonal antibodies raised to the CFn molecule, and antibodies raised to PFn, since CFn and PFn share common or homologous epitopes except for the extra type III repeat domain.

The second solid-liquid phase admixture is maintained for a second time period sufficient for the second antibodies to immunoreact with the solid phase-bound human CFn and form a second solid phase-bound immunoreactant. Maintenance times and temperatures useful for this maintenance step are similar to those described before.

The solid and liquid phases are again separated to remove any second antibodies not present in the second solid phase-bound immunoreactant, and the amount of second antibodies bound are determined. That determination is conveniently accomplished by use of a label such as an enzyme, flurochrome dye or a radiolabel operably linked to the second antibodies. Where the first, affixed antibodies and the second antibodies are induced in different animal species, such as in a goat and rabbit, respectively, the amount of second, rabbit, antibodies bound can also be determined using operably label-linked antibodies that bind specifically to antibodies of the second species, such as HRP-linked goat anti-rabbit IgG antibodies.

The amount of human plasma fibronectin (PFn) in a liquid body sample can also be determined in another embodiment of this invention. Here, two separate assays, conveniently named assay (A) and assay (B), are used.

Assay (A) is conveniently the assay for human cellular fibronectin (CFn) described above. The total amount of fibronectin present in the sample is determined in the second assay [assay (B)] as by known methods, and the difference between the amounts determined provides the amount of PFn.

An exemplary assay for total fibronectin in the sample is as follows. A second solid phase support comprised of a solid matrix as above is provided to which are affixed immunopurified antibodies raised in a host animal that immunoreact with a human fibronectin epitope in addition to those of the type III domain of CFn. Exemplary of the first antibodies are goat antibodies to rabbit PFn that are immunopurified by passage over a column of fibronectin-depleted plasma proteins conjugated to a support such as Sepharose 4B, followed by passage over and elution from an affinity column prepared from rabbit PFn conjugated to a support such as Sepharose 4B.

The liquid body sample is admixed with the solid support and maintained as described above to form a total fibronectin-containing solid phase-bound immunoreactant. After separating the solid and liquid phases, the amount of solid phase-bound immunoreactant is determined in a manner generally similar to that described before for assay (A). In preferred practice, the amount of solid phase-bound immunoreactant is determined using operably label-linked antibodies having a similar specificity to fibronectin as do the first antibodies, the heterogeneous nature of polyclonal antibodies as are obtained using the whole PFn molecule as immunogen permitting antibodies with different specificities to immunoreact and bind with the same immunogen when used as the antigen in this assay.

When performing the assay for PFn, it is preferred that known amounts from the same body fluid sample be utilized so that calculations are simplified, and concentrations in the sample can be obtained.

Detection limits in the assays described before have been found to be about 0.2 micrograms per milliliter of sample or about 10 nanograms per sample well for cellular fibronectin, and about 0.04 micrograms per milliliter of sample or about 2 nanograms per sample well for total fibronectin.

To obtain the above-described detection limits, it is preferred that ron-specific binding sites on the solid supports be blocked after the solid support is prepared. Such non-specific site blockage can be achieved by known techniques such as by admixture of an aqueous composition of a protein free from immunoreaction in the assay such as bovine serum albumin (BSA) with the solid support prior to admixture of the liquid body sample. The admixture so formed is typically maintained for the time period and at the temperature described before. The solid phase having its non-specific binding sites blocked and the liquid phase are then separated as by rinsing, and the liquid body sample is admixed.

The discussion above has included a label operably linked to antibodies. The term "operatively linked" is used herein to mean that the label molecules are linked or bonded to the antibody molecules so that antibody binding is not substantially impaired nor is the action of the label substantially impaired. Thus, antibodies containing operably linked label molecules bind to their antigen and the label molecules operate to indicate the presence of the bound antibody in an immunoreactant.

For an ELISA, typically used enzymes operably linked to antibodies as a label include horseradish peroxidase, alkaline phosphatase and the like. Each of those enzymes is used with a color-forming reagent or reagents (substrate) such as hydrogen peroxide and o-phenylenediamine; and p-nitrophenyl phosphate, respectively.

Enzyme-linked antibody (conjugate) reagents of one animal raised to the antibodies of another 10 animal such as peroxidase-linked rabbit anti-goat and goat anti-mouse antibodies, as well as phosphatase-linked rabbit anti-goat, and rabbit anti-mouse antibodies are commercially available from several suppliers such as Sigma Chemical Company of St. Louis, Mo.

Similar assays may also be carried out using fluorochrome dyes operably linked to an antibody as a label to signal the presence of antibodies bound in an immunoreaction product The fluorochrome dye is typically linked by means of an isothiocyanate group to form the conjugate. Exemplary fluorochrome dyes include fluorescein isothiocyanate (FITC), rhodamine B isothiocyanate (RITC) and tetramethylrhodamine isothiocyanate (TRITC). Conjugates such as FITC-linked rabbit anti-mouse, goat anti-mouse, goat anti-rabbit and sheep anti-morse antibodies are commercially available from several sources such as Sigma Chemical Company.

In another technique, biotin operably linked to an antibody reagent is utilized as a label to signal the presence of the immunoreactant in conjunction with avidin that is itself linked to a signalling means such as horseradish peroxidase. Biotin-linked antibody conjugates such as biotin-linked goat anti-rabbit, goat anti-mouse and rabbit anti-goat IgG's are commercially available from Polysciences, Inc. of Warrington, Pa. Avidin-FITC, avidin-RITC, avidin-peroxidase and avidin-alkaline phosphatase are also available commercially from Polysciences, Inc. for use with the biotin-linked antibody conjugates to provide the signal. Still other techniques are well known to those skilled in this art.

III. RESULTS

A. Effect of oxidant or protease treatment on fibronectin concentrations in perfusion fluid and alveolar lavage Fibronectin was not detected in the BSA-containing perfusion buffer by either ELISA or Western transfer prior to circulation through rabbit lungs. However, low levels (0.3 to 1.0 micrograms per ml) of rabbit fibronectin accumulated in the recirculating perfusate during the 30 minute equilibration period prior to experimental observation. Over the course of the ensuing 90 minutes, perfusion fluid of oxidant-injured lungs accumulated significantly greater levels of fibronectin than uninjured controls or catalase-protected lungs (Table I, below).

TABLE I

Fibronectin Levels in Perfusate and Lavage Fluid of Isolated Perfused Lungs[1]

| Group[2] | FIBRONECTIN IN: | |
|---|---|---|
| | Perfusate (µg/ml) | Lavage (µg/m) |
| Controls n = 9 | 1.5 ± 0.3 | 0.04 ± 0.01 |
| $H_2O_2$ n = 6 | 10.5 ± 1.9[3] | 0.41 ± 0.12[3] |
| $H_2O_2$ + catalase n = 4 | 1.4 ± 0.3 | 0.06 ± 0.02 |
| XO/P n = 4 | 10.9 ± 1.7[3] | 0.28 ± 0.13[3] |
| XO/P + catalase n = 4 | 1.6 ± 0.2 | 0.07 ± 0.02 |
| Trypsin n = 6 | 0.1 ± 0.0[3] | 0.07 ± 0.01[3] |

[1] Samples for assay were taken after 90 minutes of observation. Fibronectin was measured by ELISA, using rabbit plasma fibronectin standards, and data are shown in micrograms per milliliter (ug/ml).
[2] Ingredients mixed into perfusion fluid: $H_2O_2$ = hydrogen peroxide; $H_2O_2$ + catalase = hydrogen peroxide plus the enzyme catalase; XO/P = xanthine oxidase plus purine; X/OP + catalase = xanthine oxidase plus purine plus the enzyme catalase; and Trypsin = the enzyme trypsin.
[3] P less than 0.05 compared with control group.

Figure 2:
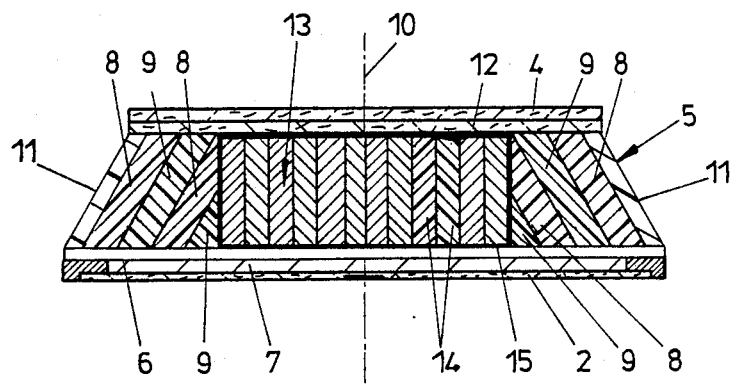
FIG. 2 contains eight graphs that illustrate the temporal relationship between perfusate fibronectin concentration measured by ELISA (upper) and increase in rabbit lung weight (lower) for (starting from left): (a) uninjured control lungs, (b) lungs exposed to $H_2O_2$ with or without catalase protection, (c) lungs exposed to $O_2^-$ with or without catalase protection, and (d) lungs exposed to trypsin.

Accelerated rates of accumulation of fibronectin in perfusion fluid of oxidant-injured lungs began in the period between 30 and 60 minutes (between 10 and 40 minutes after addition of oxidant to perfusion fluid). Edema formation, measured as increase in lung weight, generally began to occur at approximately 30 minutes. FIG. 2 plots both perfusion fluid fibronectin concentration (measured every 30 minutes) and lung weight gain (measured every 10 minutes) as a function of time.

In contrast to the oxidant injury model, continuous trypsin infusion caused edema formation between 60 and 90 minutes (40 to 70 minutes after onset of infusion). Perfusate fibronectin levels measured by ELISA decreased throughout the trypsin infusion, including the period of edema formation (FIG. 2).

Fibronectin retrieved by lavage of the alveolar space at 90 minutes was elevated in both oxidant and protease-treated groups compared with controls. Catalase pre-treatment of perfusion fluid prior to addition of oxidants prevented the increase in BAL fibronectin associated with oxidant exposure (Table I).

B. Physical characteristics of fibronectin in perfusate, lavage, and lung tissue after oxidant or protease treatment Fibronectin in perfusate and lavage of lungs treated with oxidants was intact and dimeric. Under reducing (denaturing) conditions the subunits of perfusate fibronectin from oxidant-injured lungs showed similar electrophoretic mobility to subunits of fibronectin extracted from normal rabbit lung tissue (FIG. 3a). Both migrated as single bands ($M_r$ of about 260 kDa) in low percentage gels. These bands were of a higher apparent molecular mass ($M_r$) than either of the bands formed by the subunits of rabbit plasma fibronectin ($M_r=210$ and 240 kDa). FIG. 3b shows that perfusate fibronectin is intact prior to gelatin isolation and exists as a dimer ($M_r=510$ kDa) under non-reducing conditions. Rabbit plasma fibronectin diluted in perfusion buffer and subjected to 2 mM $H_2O_2$ for 90 minutes showed no change in electrophoretic behavior.

In order to resolve small differences in electrophoretic mobility between subunits, samples of fibronectin isolated from perfusate, lavage, and rabbit plasma were subjected to prolonged electrophoresis in parallel under reducing conditions. Duration of electrophoresis was calibrated by the position of prestained molecular weight standards (Bethesda Research Laboratories, Bethesda, Md.). Resulting Western transfers for four representative lung perfusion studies are shown in FIG. 4. Under these conditions of electrophoresis, the doublet formed by rabbit plasma fibronectin became more widely separated, and the subunits of the perfusion fluid fibronectin also resolved into a doublet. Treatment with either $O_2^-$ or $H_2O_2$ caused intravascular accumulation of fibronectin of similar subunit composition. A small amount of intact fibronectin is visible in the alveolar lavage of the $H_2O_2$-injured lung represented in this figure. Additionally, the ability of catalase to prevent increased accumulation of fibronectin in perfusion fluid of $O_2^-$ or $H_2O_2$-treated lungs is confirmed in the lower panels of FIG. 3.

Fibronectin in the perfusion fluid of all trypsin-treated lungs was progressively cleaved over time. Visualization of Western-transferred fibronectin cleavage fragments from perfusion and lavage fluid was facilitated by staining with increased concentrations of anti-fibronectin antibodies. As shown in FIG. 5, the intensified staining allowed visualization of fibronectin that accumulated at low levels in the 30 minute period of recirculation prior to time =0 minutes. This fibronectin was intact and of higher molecular weight than plasma fibronectin. At later time points, it was replaced with cleavage products concomitant with administration of trypsin. Lavage fluid from protease-injured lungs also contained fibronectin fragments, and these comigrated with fragments in perfusion fluid taken at the corresponding timepoint. Fibronectin extracted from lung tissue with sodium dodecyl sulfate (SDS) was cleaved in the protease-treated group, but not in control and oxidant groups.

The fibronectin that accumulated at low levels in control and catalase-protected lungs was physically indistinguishable from oxidant-released fibronectin when examined with Western transfer using increased quantities of isolated antigen and/or anti-fibronectin antibody concentrations.

C. Effect of proteolysis of fibronectin on measurement by ELISA

Serial three-fold dilutions (10 to 0.014 ug/ml) of purified rabbit plasma fibronectin in either perfusion buffer, perfusion buffer containing lima bean trypsin inhibitor (LBTI) and N(alpha)-p-tosyl-L-lysine chloromethyl ketone (TLCK), or perfusion buffer containing trypsin alone were kept at 4 degrees C. for 2 hours. Samples containing uninhibited trypsin were then also treated with LBTI and TLCK. The final concentrations of trypsin, LBTI, and TLCK were equal to those achieved in inhibited perfusate samples from trypsin-treated lungs at 90 minutes. Fibronectin concentrations in samples containing trypsin and inhibitors averaged 97 percent, whereas concentrations in samples containing uninhibited trypsin averaged 43 percent of values for dilutions of fibronectin in perfusate alone. Western transfer examination of the samples confirmed that fibronectin exposed to trypsin without inhibitors was proteolytically degraded. In contrast, fibronectin in samples containing no trypsin or inhibited trypsin remained intact.

D. Electrophoretic examination of perfusion fluid fibronectin using anti-extra domain antibodies Antibodies to the human ED polypeptide stained fibronectin from perfusion fluid of oxidant-injured rabbit lungs but not rabbit plasma fibronectin. Staining was prevented when anti-polypeptide serum was preincubated with 750 micrograms per ml of the ED polypeptide. Only the upper band of the perfusate fibronectin doublet was stained by antiserum to the ED polypeptide. Under nonreducing conditions, the single dimeric band stained similarly with both anti-rabbit plasma fibronectin antibodies and anti-ED polypeptide antibodies (FIG. 6). Antibodies to the ED polypeptide also specifically stained higher molecular weight subunits of the intact fibronectin that accumulated at low levels in perfusion fluid of uninjured lungs.

E. Relative levels of plasma- and lung-derived fibronectin in perfusate

Lanes 5 and 6 in FIG. 6 show paired 1:9 dilutions derived from stocks of perfusate ($H_2O_2$ injury) and rabbit plasma fibronectin of equal concentrations. Equivalent dilutions of plasma and perfusate fibronectin could be clearly visualized by Western transfer through 1:27 dilutions without evidence of contamination of perfusate fibronectin by the plasma doublet, indicating that the concentration of lung-derived fibronectin occurring in the circulation due to oxidant exposure must be greater than or equal to approximately 27 times that of plasma fibronectin.

F. Effects of Oxidant or Protease Treatment on Parameters of Lung Vascular Function All lungs subjected to the cited doses of injurious agents were observed for 90 minutes of recirculation and ventilation. Net increase in lung weight over this period and BAL protein concentration were significantly increased in lungs treated with oxidants or protease compared with controls (Table II).

ing a similar specificity to fibronectin as do the first antibodies, the heterogeneous nature of polyclonal antibodies as are obtained using the whole PFn molecule as immunogen permitting antibodies with different specificities to immunoreact and bind with the same immunogen when used as the antigen in this assay.

When performing the assay for PFn, it is preferred that known amounts from the same body fluid sample be utilized so that calculations are simplified, and concentrations in the sample can be obtained.

Detection limits in the assays described before have been found to be about 0.2 micrograms per milliliter of sample or about 10 nanograms per sample well for cellular fibronectin, and about 0.04 micrograms per milliliter of sample or about 2 nanograms per sample well for total fibronectin.

To obtain the above-described detection limits, it is preferred that ron-specific binding sites on the solid supports be blocked after the solid support is prepared. Such non-specific site blockage can be achieved by known techniques such as by admixture of an aqueous composition of a protein free from immunoreaction in the assay such as bovine serum albumin (BSA) with the solid support prior to admixture of the liquid body sample. The admixture so formed is typically maintained for the time period and at the temperature described before. The solid phase having its non-specific binding sites blocked and the liquid phase are then separated as by rinsing, and the liquid body sample is admixed.

The discussion above has included a label operably linked to antibodies. The term "operatively linked" is used herein to mean that the label molecules are linked or bonded to the antibody molecules so that antibody binding is not substantially impaired nor is the action of the label substantially impaired. Thus, antibodies containing operably linked label molecules bind to their antigen and the label molecules operate to indicate the presence of the bound antibody in an immunoreactant.

For an ELISA, typically used enzymes operably linked to antibodies as a label include horseradish peroxidase, alkaline phosphatase and the like. Each of those enzymes is used with a color-forming reagent or reagents (substrate) such as hydrogen peroxide and o-phenylenediamine; and p-nitrophenyl phosphate, respectively.

Enzyme-linked antibody (conjugate) reagents of one animal raised to the antibodies of another 10 animal such as peroxidase-linked rabbit anti-goat and goat anti-mouse antibodies, as well as phosphatase-linked rabbit anti-goat, and rabbit anti-mouse antibodies are commercially available from several suppliers such as Sigma Chemical Company of St. Louis, Mo.

Similar assays may also be carried out using fluorochrome dyes operably linked to an antibody as a label to signal the presence of antibodies bound in an immunoreaction product The fluorochrome dye is typically linked by means of an isothiocyanate group to form the conjugate. Exemplary fluorochrome dyes include fluorescein isothiocyanate (FITC), rhodamine B isothiocyanate (RITC) and tetramethylrhodamine isothiocyanate (TRITC). Conjugates such as FITC-linked rabbit anti-mouse, goat anti-mouse, goat anti-rabbit and sheep anti-morse antibodies are commercially available from several sources such as Sigma Chemical Company.

In another technique, biotin operably linked to an antibody reagent is utilized as a label to signal the presence of the immunoreactant in conjunction with avidin that is itself linked to a signalling means such as horseradish peroxidase. Biotin-linked antibody conjugates such as biotin-linked goat anti-rabbit, goat anti-mouse and rabbit anti-goat IgG's are commercially available from Polysciences, Inc. of Warrington, Pa. Avidin-FITC, avidin-RITC, avidin-peroxidase and avidin-alkaline phosphatase are also available commercially from Polysciences, Inc. for use with the biotin-linked antibody conjugates to provide the signal. Still other techniques are well known to those skilled in this art.

III. RESULTS

A. Effect of oxidant or protease treatment on fibronectin concentrations in perfusion fluid and alveolar lavage Fibronectin was not detected in the BSA-containing perfusion buffer by either ELISA or Western transfer prior to circulation through rabbit lungs. However, low levels (0.3 to 1.0 micrograms per ml) of rabbit fibronectin accumulated in the recirculating perfusate during the 30 minute equilibration period prior to experimental observation. Over the course of the ensuing 90 minutes, perfusion fluid of oxidant-injured lungs accumulated significantly greater levels of fibronectin than uninjured controls or catalase-protected lungs (Table I, below).

TABLE I

Fibronectin Levels in Perfusate and Lavage Fluid of Isolated Perfused Lungs[1]

| Group[2] | FIBRONECTIN IN: | |
|---|---|---|
|  | Perfusate ($\mu g/ml$) | Lavage ($\mu g/m$) |
| Controls n = 9 | 1.5 ± 0.3 | 0.04 ± 0.01 |
| $H_2O_2$ n = 6 | 10.5 ± 1.9[3] | 0.41 ± 0.12[3] |
| $H_2O_2$ + catalase n = 4 | 1.4 ± 0.3 | 0.06 ± 0.02 |
| XO/P n = 4 | 10.9 ± 1.7[3] | 0.28 ± 0.13[3] |
| XO/P + catalase n = 4 | 1.6 ± 0.2 | 0.07 ± 0.02 |
| Trypsin n = 6 | 0.1 ± 0.0[3] | 0.07 ± 0.01[3] |

[1]Samples for assay were taken after 90 minutes of observation. Fibronectin was measured by ELISA, using rabbit plasma fibronectin standards, and data are shown in micrograms per milliliter (ug/ml).
[2]Ingredients mixed into perfusion fluid: $H_2O_2$ = hydrogen peroxide; $H_2O_2$ + catalase = hydrogen peroxide plus the enzyme catalase; XO/P = xanthine oxidase plus purine; X/OP + catalase = xanthine oxidase plus purine plus the enzyme catalase; and Trypsin = the enzyme trypsin.
[3]P less than 0.05 compared with control group.

Accelerated rates of accumulation of fibronectin in perfusion fluid of oxidant-injured lungs began in the period between 30 and 60 minutes (between 10 and 40 minutes after addition of oxidant to perfusion fluid). Edema formation, measured as increase in lung weight, generally began to occur at approximately 30 minutes. FIG. 2 plots both perfusion fluid fibronectin concentration (measured every 30 minutes) and lung weight gain (measured every 10 minutes) as a function of time.

In contrast to the oxidant injury model, continuous trypsin infusion caused edema formation between 60 and 90 minutes (40 to 70 minutes after onset of infusion). Perfusate fibronectin levels measured by ELISA decreased throughout the trypsin infusion, including the period of edema formation (FIG. 2).

Fibronectin retrieved by lavage of the alveolar space at 90 minutes was elevated in both oxidant and protease-treated groups compared with controls. Catalase pretreatment of perfusion fluid prior to addition of oxidants prevented the increase in BAL fibronectin associated with oxidant exposure (Table I).

B. Physical characteristics of fibronectin in perfusate, lavage, and lung tissue after oxidant or protease treatment Fibronectin in perfusate and lavage of lungs treated with oxidants was intact and dimeric. Under reducing (denaturing) conditions the subunits of perfusate fibronectin from oxidant-injured lungs showed similar electrophoretic mobility to subunits of fibronectin extracted from normal rabbit lung tissue (FIG. 3a). Both migrated as single bands ($M_r$ of about 260 kDa) in low percentage gels. These bands were of a higher apparent molecular mass ($M_r$) than either of the bands formed by the subunits of rabbit plasma fibronectin ($M_r=210$ and 240 kDa). FIG. 3b shows that perfusate fibronectin is intact prior to gelatin isolation and exists as a dimer ($M_r=510$ kDa) under non-reducing conditions. Rabbit plasma fibronectin diluted in perfusion buffer and subjected to 2 mM $H_2O_2$ for 90 minutes stowed no change in electrophoretic behavior.

In order to resolve small differences in electrophoretic mobility between subunits, samples of fibronectin isolated from perfusate, lavage, and rabbit plasma were subjected to prolonged electrophoresis in parallel under reducing conditions. Duration of electrophoresis was calibrated by the position of prestained molecular weight standards (Bethesda Research Laboratories, Bethesda, Md.). Resulting Western transfers for four representative lung perfusion studies are shown in FIG. 4. Under these conditions of electrophoresis, the doublet formed by rabbit plasma fibronectin became more widely separated, and the subunits of the perfusion fluid fibronectin also resolved into a doublet. Treatment with either $O_2^-$ or $H_2O_2$ caused intravascular accumulation of fibronectin of similar subunit composition. A small amount of intact fibronectin is visible in the alveolar lavage of the $H_2O_2$-injured lung represented in this figure. Additionally, the ability of catalase to prevent increased accumulation of fibronectin in perfusion fluid of $O_2^-$ or $H_2O_2$-treated lungs is confirmed in the lower panels of FIG. 3.

Fibronectin in the perfusion fluid of all trypsin-treated lungs was progressively cleaved over time. Visualization of Western-transferred fibronectin cleavage fragments from perfusion and lavage fluid was facilitated by staining with increased concentrations of anti-fibronectin antibodies. As shown in FIG. 5, the intensified staining allowed visualization of fibronectin that accumulated at low levels in the 30 minute period of recirculation prior to time =0 minutes. This fibronectin was intact and of higher molecular weight than plasma fibronectin. At later time points, it was replaced with cleavage products concomitant with administration of trypsin. Lavage fluid from protease-injured lungs also contained fibronectin fragments, and these comigrated with fragments in perfusion fluid taken at the corresponding timepoint. Fibronectin extracted from lung tissue with sodium dodecyl sulfate (SDS) was cleaved in the protease-treated group, but not in control and oxidant groups.

The fibronectin that accumulated at low levels in control and catalase-protected lungs was physically indistinguishable from oxidant-released fibronectin when examined with Western transfer using increased quantities of isolated antigen and/or anti-fibronectin antibody concentrations.

C. Effect of proteolysis of fibronectin on measurement by ELISA

Serial three-fold dilutions (10 to 0.014 ug/ml) of purified rabbit plasma fibronectin in either perfusion buffer, perfusion buffer containing lima bean trypsin inhibitor (LBTI) and N(alpha)-p-tosyl-L-lysine chloromethyl ketone (TLCK), or perfusion buffer containing trypsin alone were kept at 4 degrees C. for 2 hours. Samples containing uninhibited trypsin were then also treated with LBTI and TLCK. The final concentrations of trypsin, LBTI, and TLCK were equal to those achieved in inhibited perfusate samples from trypsin-treated lungs at 90 minutes. Fibronectin concentrations in samples containing trypsin and inhibitors averaged 97 percent, whereas concentrations in samples containing uninhibited trypsin averaged 43 percent of values for dilutions of fibronectin in perfusate alone. Western transfer examination of the samples confirmed that fibronectin exposed to trypsin without inhibitors was proteolytically degraded. In contrast, fibronectin in samples containing no trypsin or inhibited trypsin remained intact.

D. Electrophoretic examination of perfusion fluid fibronectin using anti-extra domain antibodies Antibodies to the human ED polypeptide stained fibronectin from perfusion fluid of oxidant-injured rabbit lungs but not rabbit plasma fibronectin. Staining was prevented when anti-polypeptide serum was preincubated with 750 micrograms per ml of the ED polypeptide. Only the upper band of the perfusate fibronectin doublet was stained by antiserum to the ED polypeptide. Under nonreducing conditions, the single dimeric band stained similarly with both anti-rabbit plasma fibronectin antibodies and anti-ED polypeptide antibodies (FIG. 6). Antibodies to the ED polypeptide also specifically stained higher molecular weight subunits of the intact fibronectin that accumulated at low levels in perfusion fluid of uninjured lungs.

E. Relative levels of plasma- and lung-derived fibronectin in perfusate

Lanes 5 and 6 in FIG. 6 show paired 1:9 dilutions derived from stocks of perfusate ($H_2O_2$ injury) and rabbit plasma fibronectin of equal concentrations. Equivalent dilutions of plasma and perfusate fibronectin could be clearly visualized by Western transfer through 1:27 dilutions without evidence of contamination of perfusate fibronectin by the plasma doublet, indicating that the concentration of lung-derived fibronectin occurring in the circulation due to oxidant exposure must be greater than or equal to approximately 27 times that of plasma fibronectin.

F. Effects of Oxidant or Protease Treatment on Parameters of Lung Vascular Function All lungs subjected to the cited doses of injurious agents were observed for 90 minutes of recirculation and ventilation. Net increase in lung weight over this period and BAL protein concentration were significantly increased in lungs treated with oxidants or protease compared with controls (Table II).

TABLE II

Evidence of Vascular Dysfunction[1]

| Group[2] | Change in lung Weight | Change in PAP[3] | BAL Protein Concentration[4] |
|---|---|---|---|
| Controls n = 9 | 0.5 ± 0.2 | 1.2 ± 0.3 | 0.4 ± 0.1 |
| $H_2O_2$ n = 6 | 13.5 ± 2.1[5] | 8.0 ± 1.1[5] | 2.5 ± 0.7[5] |
| $H_2O_2$ + catalase n = 4 | 0.5 ± 0.1 | 0.01 ± 0.5 | 0.7 ± 0.1 |
| XO/P n = 4 | 6.9 ± 0.9[5] | 2.4 ± 0.5 | 1.1 ± 0.3[5] |
| XO/P + catalase n = 4 | 0.85 ± 0.3 | −0.6 ± 0.9[5] | 0.4 ± 0.1 |
| Trypsin n = G | 12.9 ± 3.5[5] | 3.1 ± 0.9 | 5.4 ± 2.0[5] |

[1]Changes in lung weight and PAP represent differences between measurements at 0 and 90 minutes of observation. Values are positive unless otherwise indicated, and weight changes are given grams.
[2]See Note 2 to Table I.
[3]PAP = pulmonary artery pressure; pressure changes in centimeters measured with a water manometer.
[4]BAL was obtained after 90 minutes of observation, with proteins being measured in amounts of milligrams per milliliter.
[5]See Note 3 of Table I.

Increase in pulmonary artery pressure (PAP) over baseline was also greater in the oxidant and protease-treated groups than controls, but only significantly so in the $H_2O_2$-injury group. Pretreatment of perfusion fluid with catalase prevented disruption of all three parameters of vascular function by either $H_2O_2$ or $O_2^-$. The group treated with catalase prior to XO/P showed a small decrease in PAP compared with baseline.

SDS-PAGE of BAL fluids with elevated protein concentrations uniformly revealed that the predominant protein band comigrated with the BSA in the perfusion fluid.

G. Cellular Composition of Perfusate and Lung Tissue

In all lungs studied, the majority of non-erythrocytic cells in perfusion fluid samples were mononuclear with large round nuclei. Wright-stained smears of these cells revealed that they possessed granular cytoplasm and were similar in size to polymorphonuclear leukocytes also detected in perfusate. Hemocytometer-derived mononuclear and polymorphonuclear cell counts generally increased during perfusion experiments, but significant differences in counts and differentials did not exist between study groups at time points, as is shown in Table III, below.

TABLE III

Cells in Perfusion Fluid[1]

| | Mononuclear Cells $(10^3/ml)^3$ | | Polymorphonuclear Cells $(10^3/ml)^3$ | |
|---|---|---|---|---|
| Group[2] | 0 minutes | 90 minutes | 0 minutes | 90 minutes |
| Controls n = 9 | 59.2 ± 9.6 | 76.7 ± 10.4 | 1.5 ± 0.4 | 4.3 ± 0.5 |
| $H_2O_2$ n = 6 | 57.4 ± 10.9 | 66.3 ± 12.9 | 2.0 ± 0.2 | 4.3 ± 0.6 |
| $H_2O_2$ + catalase n = 4 | 76.0 ± 21.7 | 88.0 ± 19.9 | 2.5 ± 0.7 | 3.7 ± 0.7 |
| XO/P n = 4 | 64.1 ± 9.1 | 82.4 ± 14.1 | 1.4 ± 0.3 | 2.2 ± 0.7 |
| XO/P + catalase n = 4 | 58.8 ± 18.8 | 70.7 ± 23.5 | 1.5 ± 0.1 | 2.4 ± 0.8 |
| Trypzin n = 6 | 62.5 ± 7.4 | 84.9 ± 8.0 | 2.1 ± 0.3 | 1.9 ± 0.7 |

[1]Cell counts and differentials were performed using a hemocytometer.
[2]See note 2 of Table I.
[3]Numbers of Cells times 1000 per milliliter ($10^3$/ml).

No significant differences in morphology or cellularity could be detected between oxidant-injured and uninjured lungs by light microscopy. In contrast, frequent thinning, elongation, and rupture as alveolar septae were noted in protease injured lungs.

V. MATERIALS AND METHODS

A. Lung Preparation

1. Isolated perfused rabbit lung. Lungs from 2-2.5 kilogram New Zealand white rabbits were isolated and perfused as previously described [Shasby et al., Amer. Rev. Resp. Dis. 125:443-47 (1982)] with the following modifications: A small animal ventilator (Harvard Instruments, Millis, Mass.) and a human coronary perfusion pump (Olson Medical Products, Ashland, Mass.) were used to provide ventilation and perfusion respectively. 50 Milligrams per kilogram (mg/kg) ketamine (Parke-Davis, Morris Plains, N.J.) and 10 mg/kg zylazine (Miles Laboratories, Shawnee, Kan.) were given intramuscularly as anesthesia for tracheotomy. After establishment of ventilation [15% $O_2$, 5% $CO_2$, 80% $N_2$, respiratory rate 20, tidal volume 10 milliliters per kilogram (ml/kg), positive end-expiratory pressure 1 cm $H_2O$], 32.5 mg/kg sodium pentobarbital (Western Medical Supply, Arcadia, Calf.) was given prior to thoracotomy. All animals were anticoagulated with 1000 units of heparin (Elkins-Sinn. Cherry Hill, N.J.) injected into the right ventricle 3 minutes prior to pulmonary artery canulation. The perfusing buffer was a modified Krebs-Ringer bicarbonate buffer containing 2% bovine serum albumin (BSA) (Sigma Chemical Co., St. Louis, Mo.) warmed to 37.5 degrees C. with the pH value adjusted to between 7.3 and 7.4 after equlibration with the ventilating gas. After perfusion with 900 ml of the perfusion buffer to wash away blood elements, each pair of lungs was suspended from a manual balance in a warmed humid chamber and perfused through the pulmonary artery at a rate of 125 ml per minute with perfusate flowing by gravity from the left atrium into a 105 ml recirculating reservoir. After approximately 30 minutes of recirculation (15 minutes to prepare chamber and tubing and 15 minutes of equilibration), lung weight and pulmonary artery pressure (measured with a water manometer) were monitored and recorded every 10 minutes for 90 minutes of continuous perfusion and ventilation. Initial perfusate pH averaged 7.36 and did not differ significantly between experimental groups. The pH value at 90 minutes averaged 7.47 and also did not differ between groups.

B. Injury Models

1. Oxidant Injury. Lung vasculature was exposed to superoxide anion ($O_2^-$) by introducing the substrate 7H-imidazo(4,5-d)pyramidine (purine) (Sigma Chemical Co.) into the perfusion fluid reservoir at a concentration of 2 millimolar (mM) at 15 minutes, followed by xanthine oxidase (from bovine milk; Calbiochem, La Jolla, Calif.) at a final concentration of 0.005 units per milliliter (U/ml) at 20 minutes into the study. Exposure of blood vessels to hydrogen peroxide ($H_2O_2$) was achieved by constant infusion (Harvard infusion pump, Harvard Instruments, Millis, Mass.) of $H_2O_2$ into the perfusate reservoir at a rate of 11 nanomoles per milliliter (nmoles/ml) recirculating buffer/min beginning at 20 minutes and continuing through the conclusion of the study at 90 minutes. Catalase (from bovine liver; Sigma Chemical Co.) was added to the reservoir at 10 minutes (prior to oxidant) at a final concentration of 700 U/ml in those studies where it was utilized to consume $H_2O_2$ in perfusion fluid. $H_2O_2$ and $O_2$ were measured fluorimetrically in 1 ml aliquots of perfusion fluid taken at timepoints, using 240 micrograms (ug) para-hydroxyphenyl acetic acid, 40 ug horseradish peroxidase (HRP), and 40 ug superoxide dismutase (all from Sigma Chemical Co.) [Hyslop et al., *Anal. Biochem.* 141:280–86 (1984)]. The assay has a lower limit of detection of approximately 1 micromolar $H_2O_2$ (equivalent to 2 micromolar $O_2^-$) in perfusion fluid.

In lungs injured by $H_2O_2$ infusion, no $H_2O_2$ accumulation could be detected in the circulation throughout 90 minutes of perfusion despite significant signs of vascular dysfunction. However, when lungs were removed from the perfusion circuit, $H_2O_2$ concentration increased linearly with time and was stable for 30 minutes following completion of infusion. Similarly, neither $O_2^-$ nor its immediate dismutation product $H_2O_2$ could be detected in the perfusate at any time point during experiments in which xanthine oxidase and purine (XO/P) were added to generate $O_2^-$ intravascularly. However, after removal from the lung circulation, aliquots of perfusion fluid generated $O_2^-$ at rates commensurate with enzyme and substrate concentration. These findings were unaffected by the presence or absence of perfusate cells in the sample being assayed.

2. Protease injury. Beginning at 20 minutes, N-tosyl-L-phenylalanine chloromethyl ketone (TPCK)-treated trypsin (Sigma Chemical Co.) diluted in normal saline was constantly infused at 7.7 units per milliliter per minute (U/ml/min) into the reservoir through the end of the 90 minute recirculation. To analyze delivery of protease to the lung vasculature, samples of perfusate were assayed for trypsin activity by following the change in absorbance over time at 405 nanometers (nm) when samples or standards were incubated with the substrate N-benzyol-L-phenylalanyl-L-valyl-L-arginine-p-nitro-anilide hydrochloride (Kabi Diagnostica, Stockholm, Sweden). Lungs infused with trypsin showed linear increases in perfusate trypsin activity over time. Average 90 minute activity for this group was $356 \pm 35$ U/ml.

The dose of oxidants and trypsin used had been determined in preliminary studies to produce significant increases in lung weight and lavage protein concentration compared with controls within a 90 minute recirculation, consistent with vascular dysfunction.

3. Preparation of fluid samples. 2.5 Milliliter samples of perfusion fluid were taken from the reservoir at 0, 30, 60 and 90 minutes. At the completion of each 90 minute study a narrow bore tube was quickly inserted into the right mainstem bronchus and the lower lobe was lavaged with 5 ml of ice cold modified Gey's buffer-carbonate. The average volume recovered was 2.8 ml and did not differ significantly between study groups. Samples of perfusate and alveolar lavage (BAL) were immediately centrifuged at 11,600 rpm for 8 seconds. Cell pellets were resuspended in 2% acetic acid for counts and differentials by hemocytometer. Supernatants were snap-frozen and stored at $-70$ degrees pending assay for fibronectin by enzyme-linked immunoassay (ELISA). Prior to freezing, fluids from trypsin-injured lungs to be assayed by ELISA were immediately (within 30 seconds) made 0.2 mM with lima bean trypsin inhibitor (LBTI) (Worthington Enzymes, Freehold, N.J.) (100-fold molar excess over maximum trypsin concentrations reached in perfusate) and 6 mM N(alpha)-p-tosyl-L-lysine chloromethyl ketone (TLCK) (Sigma Chemical Co.) (3000-fold molar excess). 90 Minute perfusate samples so treated had activity in the trypsin assay approximating background activity in samples from control lungs at the same time point ($2.4 \pm 0.6$ U/ml) in inhibited samples compared with $2.0 \pm 0.2$ U/ml in control samples).

Perfusate and BAL supernatants were prepared for polyacrylamide gel electrophoresis in the presence of sodium dodecyl sulfate (SDS-PAGE) by boiling for 4 minutes with an equal volume of 10% SDS in Laemmli sample buffer (0.5 M Tris pH 6.8) preheated to 100° C. with or without 3% beta-mercaptoethanol. Laemmli, *Nature* (Lond) 227:680–85 (1970). Preliminary studies had shown that immediate boiling in SDS halted progressive proteolysis of fibronectin in tissue fluids to which protease had been added. Therefore, fluids from lungs injured with trypsin were boiled in SDS immediately (within 30 seconds) after removal from the lung circulation. Fluids from control and oxidant injured lungs, however, could be boiled in SDS at a later time after freezing without effect on the integrity of fibronectin.

Preparation of lung tissue samples. At the conclusion of each study, small sections were cut from the middle of one lower lobe, and were placed in 10% neutral-buffered formalin for light microscopy. Additionally, a piece of lung parenchyma from a lower lobe was immediately clamped with tongs precooled in liquid nitrogen. The frozen lung was homogenized for 30 seconds in a liquid nitrogen-cooled 3 ml teflon cartridge using a Mikro-dismembrator (B. Braun Instruments, FRG), yielding approximately 50 mg of frozen powder. 500 Microliters of boiling sample buffer were then added to the frozen lung powder derived from homogenization, and the resulting suspension was vortexed and boiled for an additional 4 minutes. Insoluble lung material was then pelleted by centrifugation, and samples of the supernatant subjected to SDS-PAGE.

5. Examination of fibronectins by Western transfer. Electrophoresis was performed in low percentage or gradient SDS-polyacrylamide gels. The proteins in the gels were electrophoretically transferred to nitrocellulose sheets (Millipore Co., Bedford, Mass.) as described by Towbin et al. *Proc. Nat. Acad. Sci. USA* 76(9):4350–54 (1979). After transfer, the sheets were blocked with 3% gelatin in Tris-buffered saline pH 7.4 (TBS) for 30 minutes and then soaked overnight in 1% gelatin in TBS containing goat anti-fibronectin antibodies. After washing in TBS containing 0.05% Tween 20 [polyoxyethylene (20) sorbitan monolaurate], the sheets were soaked for 90 minutes in 1% gelatin in TBS containing horseradish peroxidase (HRP)-conjugated swine antibodies to goat IgG. The sheets were washed prior to visualization of immunoreactive protein bands by incubation with 0.05% $H_2O_2$ and 0.5 mg/ml HRP Color Development Reagent (Bio Rad, Richmond, Calif.) in TBS containing 17% methanol for 30 minutes.

6. Isolation of fibronectins. Fibronectin (Fn) was purified from rabbit plasma, pooled lung perfusate, human plasma, and conditioned media (Dulbecco's modified Eagle's essential medium containing 10% fetal bovine serum) from confluent GM-1380 human fibroblasts by affinity chromatography on gelatin sepharose. Engvall et al., *Int. J. Cancer* 20:1-5 (1977).

In order to compare electrophoretic mobility of fibronectins contained in small samples of lung perfusate, lavage, and tissue, distortions in electrophoretic mobility due to other proteins was minimized by isolating fibronectin using small non-limiting quantities of gelatin-agarose beads (Pierce Chemical Co., Rockford, Ill.). Tamkun, et al. *J. Biol. Chem.* 258(7):4641-47 (1983). 100 Microliters of perfusate or lavage were shaken with 40 microliters of packed gelatin beads for 15 minutes at room temperature, pelleted by centrifugation, and washed 3 times with PBS containing 2 mM EDTA prior to elution with 100 microliters of sample buffer. Lung tissue fibronectin was isolated by first shaking approximately 20 mg of lyophylized powder [Schraufstatter et al., *J. Clin. Invest.* 73:1175-84 (1984)] from perfused (bloodless) rabbit lung tissue with one ml of 2 molar urea, 10 mg/ml porcine intestinal heparin (Sigma Chemical Co.), and 2 mM phenylmethylsulfonyl fluoride (PMSF) in PBS at room temperature for 4 hours. Bray, et al. *Science* 214:793-95 (1981). The supernatant from the resulting suspension was diluted 10 fold with PBS and shaken with gelatin-agarose beads prior to washing and elution with sample buffer.

C. Polypeptides and Antibodies

1. Synthesis of human fibronectin extra domain peptide. The 90 amino acid extra type III domain of human fibronectin contains a region occuring at about position 36 to about position 60 amino acid residues from its amino-terminal end in which there is a relative absence of sequence homology with other type III repeats. Kornblihtt et al. *EMBO J.* 4(7):1755-59 (1985). The 19 amino acid residue polypeptide having the sequence, from left to right and in the direction from amino-terminus to carboxy-terminus, of ELFPAPDGEEDTAELQGGC [ED polypeptide] was synthesized using solid phase methodology on an Applied Biosystems Model 438 peptide synthesizer (Applied Biosystems, Foster City, Calif.). Merrifield, *J. Am. Chem. Soc.* 85:2149-54 (1963). The N-terminal 17 amino acids of that polypeptide represent a region of the extra domain running 45 to 61 amino acids from its amino-terminus. The carboxy terminal glycine and cysteine were added for linkage to the solid phase during synthesis. A longer polypeptide from the same region having the amino acid residue sequence VTYSSPEDGIHELFPAPDGEEDTAELQGGC was similarly prepared in which the carboxy-terminal two residues as are discussed above.

The polypeptides migrated greater than 90% in a single peak when subjected to high performance liquid chromatography using a Vydac C18 column (Western Analytical Products, Temecula, Calif.). To confirm amino acid compositions, the polypeptides were hydrolyzed in 6 N hydrochloric acid for 24 hours at 110 degrees C., dried overnight, and then applied to a Beckman 121-M Amino Acid Analyzer column (Beckman Instruments, Fullerton, Calif.). The individual amino acid contents conformed 99.9% with the desired peptide composition.

2. Anti-fibronectin antibodies. Antibodies to rabbit plasma fibronectin were raised in a goat by weekly multiple intradermal injections of 100 micrograms of purified antigen emulsified in Freund's adjuvant (Difco Laboratories, Detroit, Mich.). Antibodies to the extra type III domain of human fibronectin were similarly raised in goats by weekly intradermal injections in adjuvant of 150 micrograms of the extra domain peptide (ED peptide) coupled to keyhole limpet hemocyanin (Pacific Bio-Marine, Venice, Calif.) by the glutaraldehyde method. Dockray, *Regulatory Peptides*, 1:169-86 (1980). Antibody titers specific for the ED peptide were checked by ELISA. Engvall, et al., *Arch. Biochem. Biophys.*, 222(2):649-58, (1983).

To insure that the anti-ED peptide antibodies were in fact reactive with non-hepatic (cellular) but not hepatic (plasma) fibronectin, equal quantities of protein from stocks of fibronectins (Fn's) purified from human plasma and GM-1380 cultured human fibroblast media were subjected to sodium dodecyl sulfate-polyacrylamide gel electrophonesis (SDS-PAGE) with Western transfer. Protein concentrations were determined with BCA protein assay reagent kit (Pierce Chemical Co., Rockford, Ill.) using bovine serum albumin (BSA) as a standard. Staining was achieved with goat anti-ED polypeptide antibodies, goat anti-ED polypeptide antibodies preincubated with 750 micrograms per ml of ED polypeptide, or goat anti-rabbit plasma fibronectin antibodies (crossreactive with human and bovine fibronectins).

Figure 3:
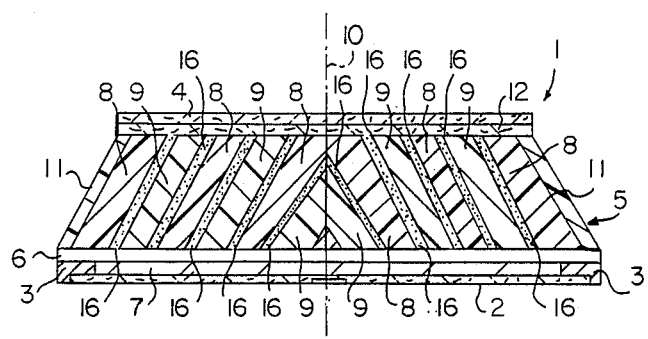
FIG. 3 illustrates a comparison of fibronectins. Rabbit fibronectins from different sources were subjected to SDS-PAGE, Western transfer using anti-rabbit plasma fibronectin antibodies, and visualizations as discussed in MATERIALS AND METHODS.
Figure 1:
Figure 2:
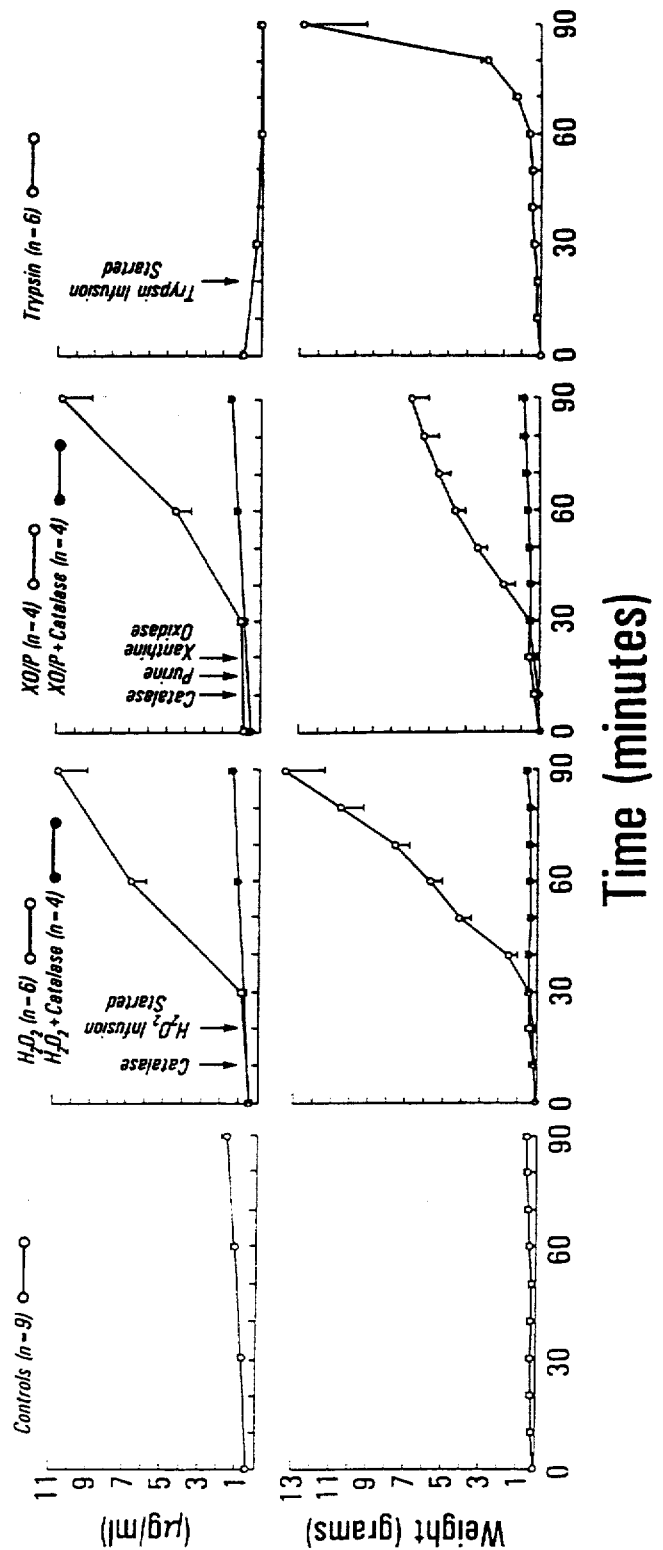

As seen in FIG. 1, the anti-ED polypeptide antibodies did not react with human plasma fibronectin, but did react specifically with fibronectin isolated by gelatin affinity chromatography from human fibroblast conditioned media. Additionally, the media, which contained fetal calf serum, was noted to contain fibronectin (Fn) bands that comigrated with bovine plasma fibronectin and did not react with anti-ED polypeptide antibodies When GM-1380 fibroblasts were grown in DMEM with 10 percent fetal calf serum which had previously been absorbed free of bovine PFn lay passage over a gelatin-sephorose affinity column, Fn subsequently isolated from the medium migrated in SDS-PAGE as a single broad band with approximate molecular weight of 260 kDa. Western blotting of this Fn with anti-ED polypeptide antibodies revealed reactivity with the higher molecular weight subunits of the fibroblast Fn (FIG. 3). Again, the anti-ED polypeptide antibodies did not react with any subunits of human plasma or fetal calf serum Fn's.

D. ELISA Assays

1. Measurement of fibronectin in fluid samples. A quantitative non-competitive enzyme-linked immunosorbant assay (ELISA) was constructed using rabbit plasma fibronectin standards, Engvall, *Meth. Enz.*, 70:419-39, (1980). Wells of microtiter plates were first coated with goat anti-rabbit plasma fibronectin antibodies immunopurified as described [Ruoslahti et. al., *Meth. Enz.*, 82:803-30, 1982] and diluted in 0.1 M NaHCO₃ Next, standards and samples, both diluted in perfusion buffer (2 percent BSA) were applied. Finally, immunopurified goat anti-rabbit plasma fibronectin antibodies conjugated to alkaline phosphatase (from bovine intestinal mucosa; Sigma Chemical Co.) with glutaraldehyde [Engvall, *Meth. Enz.*, 70:419-39, (1980)

were applied. P-Nitrophenyl phosphate (Sigma Chemical Co.) at 1 mg/ml in 1M diethanolamine at pH 9.8 was utilized as substrate for color development. A sigmoid standard curve was established by the relationship between the log of the concentration of rabbit plasma fibronectin standards or sample dilutions, and the absorbance reading of 405 nm after 120 minutes of color development.

2. CFn-Specific ELISA

ELISA studies showing the specificity of the present anti-polypeptide antibodies were conducted using purified human CFn as standard. Purified human CFn for standards was obtained by growing human GM-1380 fibroblasts in DMEM with 10 percent fetal calf serum previously depleted of calf serum Fn (PFn) by passage over a gelatin-Sepharose column. The GM-1380 cells were obtained from the Human Genetic Mutant Cell Repository Institute for Medical Research, Camden, N.J. Conditioned media containing 0.1 mM PMSF was dialyzed versus PBS containing PMSF prior to isolation of CFn by gelatin chromatography. The bound CFn was eluted with 1.0 M sodium bromide, 0.5 M sodium acetate, at pH 5, Mosher et al., *J. Biol. Chem.* 255(3):1181–1188 (1980). Purity of the isolated CFn was determined by the presence of a single broad band at approximately 260 kDa when the isolated protein was subjected to SDS-PAGE under reducing conditions followed by staining with Coomassie Blue or Western blotting with anti-PFn antibodies.

The assays for CFn and total Fn employ immunopurified goat antibodies. Goat anti-ED polypeptide antibodies were immunopurified by passage of immune goat serum over a column of ED-polypeptide conjugated to Sepharose (Pharmacia Fine Chemicals, Piscataway, N.J.). Elution of specific antibodies was accomplished with 50 mM glycine buffer at pH 2.6. Engvall, *Meth. Enz.* 70:419–39 (1980). The peak fractions were neutralized with Tris base and dialyzed versus distilled water prior to lyophylization. Goat antibodies to rabbit PFn (crossreactive with human PFn) were prepared by passage of immune goat serum first over a column of Fn-depleted rabbit plasma proteins conjugated to Sepharose followed by absorption and elution as above from a column of rabbit PFn-Sepharose. Those antibodies were also dialyzed and lyophylized.

Alkaline phosphatase-conjugated anti-rabbit PFn antibodies were prepared by the method of Engvall, *Meth. Enz.* 70:419–39 (1980). Briefly 1.5 mg of calf intestinal alkaline phosphatase (Sigma Chemical Co., St. Louis, Mo.) and 0.5 mg immunopurified anti-rabbit PFn in a total volume of 0.4 ml were dialyzed versus 1 liter of PBS for about eighteen hours (overnight). Glutaraldehyde at a final concentration of 0.02 percent (v/v) was admixed with the dialyzed mixture and maintained at room temperature for 3 hours, followed by dialysis against 0.1 M Tris pH 8. BSA and sodium azide were added at 10 mg/ml and 0.02 percent final concentrations respectively, and the conjugate was stored in the dark at 4 degrees C.

The ELISA for human CFn was performed as follows. 50 Microliters of immunopurified goat anti-ED polypeptide antibodies at 30 micrograms per milliliter (ug/ml) in 0.1 NaHCO$_3$ were pipetted into wells of 96-well flat-bottomed microtiter plates and incubated in a moist chamber overnight at room temperature. The wells were then washed twice with 0.9 percent NaCl with 0.05 percent Tween 20, followed by incubation with 150 microliters per well of 2 percent BSA in 0.1 M NaHCO$_3$ at 37 degrees for 2 hours. The wells are again washed twice and then coated rapidly with 25 microliters per well of PBS (pH 7.2) with 0.05 percent Tween 20 (incubation buffer) t keep wells moist during sample application. 50 Microliters of fibroblast-derived CFn standards or samples diluted in 2 percent BSA/PBS were then applied to duplicate wells and incubated at 37 degrees for 3 hours. The wells were then washed 3 times, followed by addition cf 50 microliters of anti-rabbit PFn-alkaline phosphatase conjugate diluted 1:250 in incubation tuffer from the stock solution. After 4 hours of incubation at room temperature, the wells were washed 3 times and 100 microliters per well p-nitrophenylphosphate at 1 mg/ml in 1 M diethanolamine tuffer at pH 9.8 were added. After 30 minutes of color development at room temperature, the microtiter plates were read at 405 nm.

A sigmoid standard curve was established by the relationship between the log of the concentration of CFn standards or sample dilutions and the absorbance reading. When wells were coated with 25 microliters of incubation buffer containing 2.5 micrograms of the 19 amino acid ED polypeptide per ml instead of incubation buffer alone, the absorbance signal was abolished, indicating antibody specificity for the ED polypeptide region of human CFn.

The ELISA for total Fn can be performed simultaneously with that for CFn, using the same CFn dilutions as standards and the same anti-PFn-alkaline phosphatase conjugate. For small numbers of samples, the two assays can be performed on the same 96-well plate. The only difference in performance of the assay for total Fn is that the initial solid phase-bound antibody is immunopurified goat anti-PFn at a concentration of 5 micrograms per ml of 0.1M NaHCO$_3$. Mixing of samples with ED-polypeptide in this assay had no effect on absorbance readings, conforming with the fact that antibodies raised to Fn isolated from plasma recognize the entire PFn molecule.

When equivalent concentrations of Fn isolated either from human plasma or from human fibroblast media were subjected to ELISA for total Fn, similar curves were generated, as the two Fn's are detected equally by anti-PFn antibodies. However, when the same paired set of dilutions was subjected to the CFn ELISA, the PFn curve was greatly diminished in comparison with the CFn curve. The small signal seen at low dilutions of PFn was peptide-inhibitable, indicating that it arose from small quantities of CFn contained in the total plasma-isolated Fn. When concentrated stocks of pooled plasma-isolated Fn were subjected to the CFn ELISA, displaced curves were generated that have similar slopes to the CFn standard curve, and can be ablated by co-incubation of antigen with ED-polypeptide. This again points to the presence of relatively small (approximately 1 part in 750 to 1000) quantities of CFn in the total Fn isolated from plasma by gelatin chromatography.

To demonstrate the dual assay in practice, a sample of plasma (acid citrate dextrose anticoagulated) from a normal (free from known tumor and tissue injury) female 30 year-old volunteer was subjected to the assay. Curves were obtained by subjecting dilutions of her plasma to either the CFn or total Fn assays. Using the same set of CFn standards for both arms of the assay, dilutions of her plasma that fell in the steep portion of the standard curve yielded values of 206 micrograms per ml total Fn and 0.270 micrograms per ml CFn. The detection limits of the two ELISA's are approximately 0.2 micrograms per ml or 10 nanograms per sample well for CFn and 0.04 micrograms per ml or 2 nanograms per sample well for total Fn.

E. Additional Matters

1. Measurement and characterization of total BAL protein. Total protein in BAL samples was measured by the method of Lowry [Lowry, et al., *J. Biol. Chem.*, 193:265-75, 1951], using BSA as a standard. Additionally, 2 microliters of BAL fluid from each study were subjected to SDS/PAGE using a 5-20 percent SDS-acrylamide gradient under both reducing and nonreducing conditions. Visualization of resulting protein bands was achieved by Coomassie Brilliant Blue staining.

2. Data presentation and statistics. Values were expressed as mean ± standard error of the means (SEM). Statistical analyses were performed by use of the Student's two-tailed t test. p Values less than 0.05 were considered significant.

The present invention has been described with respect to preferred embodiments. It will be clear to those skilled in the art that modifications and/or variations of the disclosed subject matter can be made without departing from the scope of the invention set forth herein.

What is claimed is:

1. A method of assaying for the concentration of human cellular fibronectin in the blood, plasma or serum of a patient, comprising the steps of:
    (a) providing a solid phase support comprising antibodies affixed to a solid matrix, said antibodies immunoreacting with:
        (i) a synthetic polypeptide containing about 10 to 25 amino acid residues that correspond substantially in sequence to a portion of the amino acid residue sequence of the 90 amino acid residue extra type III domain of human cellular fibronectin from about position 36 to about position 60 from the amino-terminus,
        (ii) denatured human cellular fibronectin, and
        (iii) native human cellular fibronectin, but does not substantially immunoreact with:
        (iv) native human plasma fibronectin, and
        (v) denatured human plasma fibronectin;
    (b) admixing a predetermined amount of a liquid sample of said blood, plasma or serum to be assayed with said solid phase support to form a solid-liquid phase admixture;
    (c) maintaining said solid-liquid phase admixture for a predetermined time period sufficient for human cellular fibronectin present in the sample to immunoreact with said solid phase-affixed antibody to form a solid phase-bound immunoreactant and a liquid phase depleted of human cellular fibronectin;
    (d) separating the solid and liquid phases formed in step (c); and
    (e) determining the amount of solid phase-bound immunoreactant formed in step (c), and thereby the amount of human cellular fibronectin present in the assayed sample.

2. The method according to claim 1 wherein said synthetic polypeptide has a sequence, from left to right and in the direction from amino-terminus to carboxy-terminus, of
    (a) ELFPAPDGEEDTSELQG, or
    (b) TYSSPEDGIHELFPAPDGEEDTAELQG.

3. The method according to claim 1 wherein said determination of the concentration of solid phase-bound immunoreactant of step (e) is made by admixing second antibodies that immunoreact with the solid phase-bound human cellular fibronectin to form a second solid-liquid phase admixture;
    maintaining said second solid-liquid phase admixture for a second time period sufficient for the second antibodies to immunoreact with the solid phase-bound human cellular fibronectin and form a second solid phase-bound immunoreactant;
    separating the solid and liquid phases; and
    determining the amount of second antibodies bound in said immunoreactant.

4. The method according to claim 3 wherein said second antibodies include an operatively linked labeling means.

5. The method according to claim 3 wherein said synthetic polypeptide has a sequence, from left to right and in the direction from amino-terminus to carboxy-terminus, of
    (a) ELFPAPDGEEDTSELQG, or
    (b) TYSSPEDGIHELFPAPDGEEDTAELQG.

6. A method of assaying for tissue injury in a patient, that comprises:
    (a) determining the concentration of cellular fibronectin present in an aliquot of a liquid body sample of blood, plasma or serum from the patient by:
        (1) providing a solid phase support comprising antibodies affixed to a solid matrix, said antibodies immunoreacting with:
            (i) a synthetic polypeptide containing about 10 to 25 amino acid residues that correspond substantially in sequence to a portion of the amino acid residue sequence of the 90 amino acid residue extra type III domain of human cellular fibronectin from about position 36 to about position 60 from the amino terminus,
            (ii) denatured human cellular fibronectin, and
            (iii) native human cellular fibronectin, but not substantially immunoreacting with:
            (v) native human plasma fibronectin, and
            (v) denatured human plasma fibronectin;
        (2) admixing said aliquot with said solid phase support to form a solid-liquid phase admixture;
        (3) maintaining said solid-liquid phase admixture for a predetermined time period sufficient for cellular fibronectin present in said aliquot to immunoreact with said solid-phase bound immunoreactant and a liquid phase depleted of cellular fibronectin;
        (4) separating the solid and liquid phase formed in step (3); and
        (5) determining the amount of solid phase-bound immunoreactant formed in step (3), and thereby the concentration of cellular fibronectin present in the assayed sample aliquot; and
    (b) comparing said determined concentration with the concentration of cellular fibronectin in healthy, non-injured controls, an elevation of cellular fibronectin concentration in said patient's body sample indicating tissue injury in said patient.

7. The method according to claim 6, wherein said tissue injury is an endothelial cell injury.

8. The method according to claim 6, wherein said elevated cellular fibronectin concentration is an indication of intravascular injury.

9. The method according to claim 6 wherein said synthetic polypeptide has a sequence, from left to right and in the direction from amino-terminus to carboxy-terminus, of
    (a) ELFPAPDGEEDTSELQG, or
    (b) TYSSPEDGIHELFPAPDGEEDTAELQG.

* * * * *

UNITED STATES PATENT AND TRADEMARK OFFICE
CERTIFICATE OF CORRECTION

PATENT NO. : 4,980,279

DATED : Dec. 25, 1990

INVENTOR(S) : John H. Peters, Mark H. Ginsberg, Charles G. Cochrane

It is certified that error appears in the above-identified patent and that said Letters Patent is hereby corrected as shown below:

On the cover page and on drawing sheets "1 of 2" and "2 of 2", kindly delete Figures 1, 2, and 3 and replace them with Figures 1, 2, 3A, 3B, 4, 5, 6A, and 6B attached hereto.

Signed and Sealed this

Twenty-third Day of January, 1996

Attest:

BRUCE LEHMAN

Attesting Officer

Commissioner of Patents and Trademarks

| Plas Cell | Plas Cell | Plas Cell |
|---|---|---|
| | |  |
| Anti-Peptide | Blocked Anti-Peptide | Anti-Plasma Fibronectin |

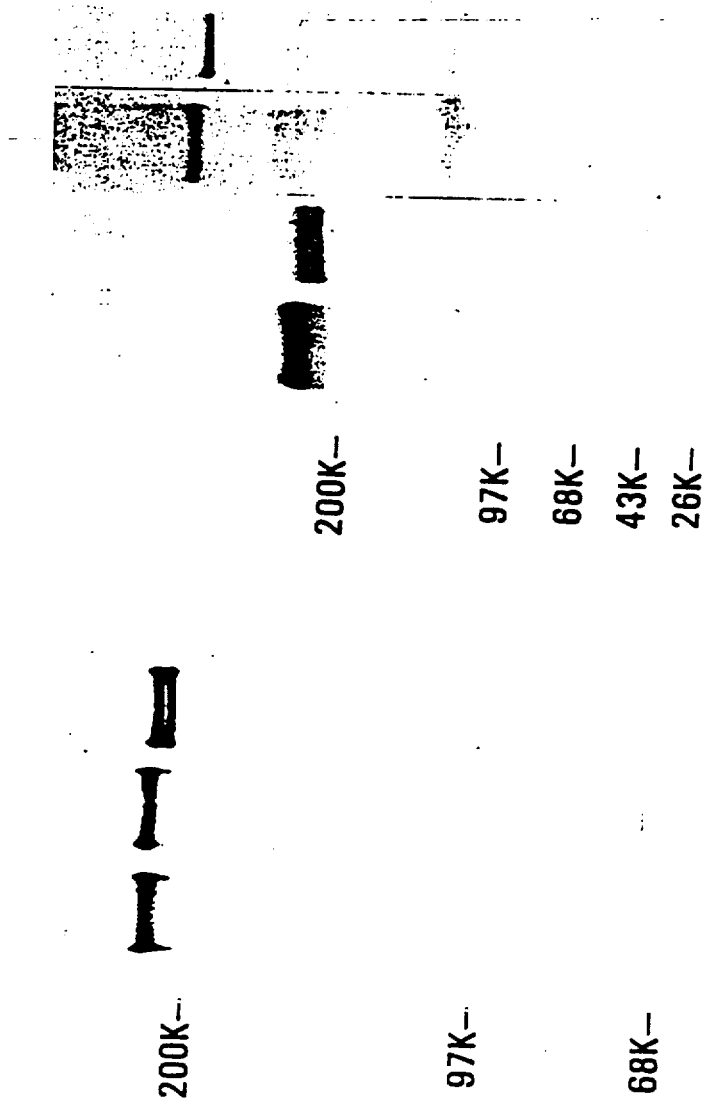

| Treatment | Xanthine Oxidase + Purine | $H_2O_2$ Infusion |
|---|---|---|

−Catalase

| | PLAS FN | PERFUSATE | | | BAL | PLAS FN | PERFUSATE | | | BAL |
|---|---|---|---|---|---|---|---|---|---|---|
| Time (minutes) | 0 | 30 | 60 | 90 | 90 | 0 | 30 | 60 | 90 | 90 |

+Catalase

| | PLAS FN | PERFUSATE | | | BAL | PLAS FN | PERFUSATE | | | BAL |
|---|---|---|---|---|---|---|---|---|---|---|
| Time (minutes) | 0 | 30 | 60 | 90 | 90 | 0 | 30 | 60 | 90 | 90 |

FIG. 4

200K—

97K—
68K—
43K—
26K—

```
PLAS   PERFUSATE   BAL LUNG
 FN   0  30  60  90   90  90
```

Minutes

FIG. 5

UNITED STATES PATENT AND TRADEMARK OFFICE
CERTIFICATE OF CORRECTION

Page 1 of 1

PATENT NO.      : 4,980,279
DATED           : December 25, 1990
INVENTOR(S)     : John H. Peters, Mark H. Ginsberg and Charles G. Cochrane It is certified that error appears in the above-identified patent and that said Letters Patent is hereby corrected as shown below:

<u>Column 1,</u>
Line 6, insert:
-- This invention was made with government support under Grant No. HL 28235 from the National Institutes of Health. The U.S. government may have certain rights in the invention. --

Signed and Sealed this

Twenty-first Day of May, 2002

Attest:

Attesting Officer

JAMES E. ROGAN
*Director of the United States Patent and Trademark Office*